(12) United States Patent
Estey et al.

(10) Patent No.: US 11,077,089 B2
(45) Date of Patent: Aug. 3, 2021

(54) ORAL COMPOSITIONS DELIVERING THERAPEUTICALLY EFFECTIVE AMOUNTS OF CANNABINOIDS

(71) Applicant: Per Os Biosciences, LLC, Hunt Valley, MD (US)

(72) Inventors: Robert Estey, Hunt Valley, MD (US); William O. Brisben, Stuart, FL (US)

(73) Assignee: Per Os Biosciences, LLC, Hunt Valley, MD (US)

( * ) Notice: Subject to any disclaimer, the term of this patent is extended or adjusted under 35 U.S.C. 154(b) by 0 days.

(21) Appl. No.: 16/988,041

(22) Filed: Aug. 7, 2020

(65) Prior Publication Data

US 2021/0008027 A1    Jan. 14, 2021

Related U.S. Application Data

(62) Division of application No. 15/615,521, filed on Jun. 6, 2017, now Pat. No. 10,765,658.

(60) Provisional application No. 62/353,420, filed on Jun. 22, 2016.

(51) Int. Cl.
| | | |
|---|---|---|
| *A61K 31/352* | (2006.01) | |
| *A61K 31/05* | (2006.01) | |
| *A61K 36/185* | (2006.01) | |
| *A61K 9/20* | (2006.01) | |
| *A61K 9/00* | (2006.01) | |
| *A61K 9/68* | (2006.01) | |
| *A61K 31/70* | (2006.01) | |
| *A61K 47/10* | (2017.01) | |
| *A61K 47/24* | (2006.01) | |
| *A61K 47/36* | (2006.01) | |

(52) U.S. Cl.
CPC .......... *A61K 31/352* (2013.01); *A61K 9/0056* (2013.01); *A61K 9/0058* (2013.01); *A61K 9/2018* (2013.01); *A61K 9/2095* (2013.01); *A61K 31/05* (2013.01); *A61K 31/70* (2013.01); *A61K 36/185* (2013.01); *A61K 47/10* (2013.01); *A61K 47/24* (2013.01); *A61K 47/36* (2013.01)

(58) Field of Classification Search
CPC .... A61K 31/352; A61K 9/0056; A61K 47/26; A61K 47/38
See application file for complete search history.

(56) References Cited

U.S. PATENT DOCUMENTS

| | | |
|---|---|---|
| 4,370,350 A | 1/1983 | Fisher et al. |
| 4,753,805 A | 6/1988 | Cherukuri et al. |
| 4,975,270 A | 12/1990 | Kehoe |
| 5,121,329 A | 6/1992 | Crump |
| 5,127,037 A | 6/1992 | Bynum |
| 5,204,055 A | 4/1993 | Sachs et al. |
| 5,252,264 A | 10/1993 | Forderhase et al. |
| 5,340,656 A | 8/1994 | Sachs et al. |
| 5,387,380 A | 2/1995 | Cima et al. |
| 5,490,882 A | 2/1996 | Sachs et al. |
| 5,490,962 A | 2/1996 | Cima et al. |
| 5,518,680 A | 5/1996 | Cima et al. |
| 5,711,961 A | 1/1998 | Reiner et al. |
| 5,717,599 A | 2/1998 | Menhennett et al. |
| 5,851,465 A | 12/1998 | Bredt |
| 5,866,179 A | 2/1999 | Testa |
| 5,869,170 A | 2/1999 | Cima et al. |
| 5,879,489 A | 3/1999 | Burns et al. |
| 5,934,343 A | 8/1999 | Gaylo et al. |
| 5,940,674 A | 8/1999 | Sachs et al. |
| 6,007,318 A | 12/1999 | Russell et al. |
| 6,146,567 A | 11/2000 | Sachs et al. |
| 6,165,406 A | 12/2000 | Jang et al. |
| 6,193,923 B1 | 2/2001 | Leyden et al. |
| 6,200,508 B1 | 3/2001 | Jacobson et al. |
| 6,213,168 B1 | 4/2001 | Gaylo et al. |
| 6,322,828 B1 | 11/2001 | Athanikar et al. |
| 6,336,480 B2 | 1/2002 | Gaylo et al. |
| 6,344,222 B1 | 2/2002 | Cherukuri et al. |
| 6,363,606 B1 | 4/2002 | Johnson, Jr. et al. |
| 6,375,874 B1 | 4/2002 | Russell et al. |
| 6,508,971 B2 | 1/2003 | Leyden et al. |
| 6,530,958 B1 | 3/2003 | Cima et al. |
| 6,547,994 B1 | 4/2003 | Monkhouse et al. |
| 6,582,738 B2 | 6/2003 | Gubler |
| 6,596,224 B1 | 7/2003 | Sachs et al. |
| 6,772,026 B2 | 8/2004 | Bradbury et al. |
| 6,850,334 B1 | 2/2005 | Gothait |
| 6,905,645 B2 | 6/2005 | Iskra |
| 6,945,638 B2 | 9/2005 | Teung et al. |
| 6,989,115 B2 | 1/2006 | Russell et al. |

(Continued)

FOREIGN PATENT DOCUMENTS

| | | |
|---|---|---|
| EP | 0151344 | 8/1985 |
| EP | 1631440 | 3/2006 |

(Continued)

OTHER PUBLICATIONS

Abbadie et al., Chemokines and pain mechanisms. Brain Res Rev. Apr. 2009;60(1):125-34.

(Continued)

*Primary Examiner* — James D. Anderson

(74) *Attorney, Agent, or Firm* — Mintz Levin Cohn Ferris Glovsky and Popeo, P.C.; Nicholas A. Zachariades

(57) ABSTRACT

Oral compositions provide delivery of cannabinoids to a subject. The oral compare chewable, fast- or slow-dissolving once placed in the mouth of a subject.

16 Claims, 32 Drawing Sheets

(32 of 32 Drawing Sheet(s) Filed in Color)

(56) References Cited

U.S. PATENT DOCUMENTS

| | | |
|---|---|---|
| 7,101,579 B2 | 9/2006 | Athanikar et al. |
| 7,208,186 B2 | 4/2007 | Norman et al. |
| 7,220,380 B2 | 5/2007 | Farr et al. |
| 7,291,002 B2 | 11/2007 | Russell et al. |
| 7,351,438 B2 | 4/2008 | Sozzi et al. |
| 7,365,129 B2 | 4/2008 | Kramer et al. |
| 7,435,368 B2 | 10/2008 | Davidson et al. |
| 7,455,804 B2 | 11/2008 | Patel et al. |
| 7,815,898 B2 | 10/2010 | Savica |
| 7,828,022 B2 | 11/2010 | Davidson et al. |
| 8,017,055 B2 | 9/2011 | Davidson et al. |
| 8,828,411 B2 | 9/2014 | Yoo et al. |
| 8,888,480 B2 | 11/2014 | Yoo et al. |
| 8,906,429 B1 * | 12/2014 | Kolsky .............. A61K 9/0056 424/725 |
| 9,023,322 B2 | 5/2015 | Van Damme et al. |
| 9,314,429 B2 | 4/2016 | Jacob et al. |
| 9,339,489 B2 | 5/2016 | Jacob et al. |
| 9,433,601 B2 | 9/2016 | Van Damme et al. |
| 9,744,128 B2 | 8/2017 | Bachmann et al. |
| 10,463,612 B2 | 11/2019 | Bachmann et al. |
| 10,765,658 B2 | 9/2020 | Estey et al. |
| 2001/0017085 A1 | 8/2001 | Kubo et al. |
| 2001/0028471 A1 | 10/2001 | Hirokazu |
| 2002/0015728 A1 | 2/2002 | Payumo et al. |
| 2002/0033548 A1 | 3/2002 | Brodkin et al. |
| 2002/0064745 A1 | 5/2002 | Schulman et al. |
| 2002/0079601 A1 | 6/2002 | Russell et al. |
| 2002/0114652 A1 | 8/2002 | Morozumi et al. |
| 2002/0125592 A1 | 9/2002 | Schulman et al. |
| 2003/0143268 A1 | 7/2003 | Pryce Lewis et al. |
| 2003/0198677 A1 | 10/2003 | Pryce Lewis et al. |
| 2004/0003738 A1 | 1/2004 | Imiolek et al. |
| 2004/0003741 A1 | 1/2004 | Iskra et al. |
| 2004/0004303 A1 | 1/2004 | Iskra |
| 2004/0004653 A1 | 1/2004 | Pryor et al. |
| 2004/0005182 A1 | 1/2004 | Gaylo et al. |
| 2004/0005360 A1 | 1/2004 | Wang et al. |
| 2004/0012112 A1 | 1/2004 | Davidson et al. |
| 2004/0028772 A1 | 2/2004 | Andersen |
| 2004/0112523 A1 | 6/2004 | Crom et al. |
| 2004/0118309 A1 | 6/2004 | Fedor et al. |
| 2004/0141024 A1 | 7/2004 | Silverbrook |
| 2004/0141025 A1 | 7/2004 | Silverbrook |
| 2004/0141030 A1 | 7/2004 | Silverbrook |
| 2004/0141043 A1 | 7/2004 | Silverbrook |
| 2004/0143359 A1 | 7/2004 | Yogo et al. |
| 2004/0145628 A1 | 7/2004 | Silverbrook |
| 2004/0145781 A1 | 7/2004 | Silverbrook |
| 2004/0183796 A1 | 9/2004 | Velde et al. |
| 2004/0194793 A1 | 10/2004 | Lindell et al. |
| 2004/0225398 A1 | 11/2004 | Silverbrook |
| 2004/0243133 A1 | 12/2004 | Materna |
| 2004/0252174 A1 | 12/2004 | Baxter et al. |
| 2004/0262797 A1 | 12/2004 | Schulman et al. |
| 2004/0265413 A1 | 12/2004 | Russell et al. |
| 2005/0059757 A1 | 3/2005 | Bredt et al. |
| 2005/0061241 A1 | 3/2005 | West et al. |
| 2005/0069784 A1 | 3/2005 | Gothait et al. |
| 2005/0090468 A1 | 4/2005 | Jarvinen et al. |
| 2005/0104241 A1 | 5/2005 | Kritchman et al. |
| 2005/0179721 A1 | 8/2005 | Jones et al. |
| 2005/0204939 A1 | 9/2005 | Krejci |
| 2005/0247216 A1 | 11/2005 | Reichwein et al. |
| 2006/0003050 A1 | 1/2006 | Nissen |
| 2006/0030964 A1 | 2/2006 | Silverbrook |
| 2006/0035034 A1 | 2/2006 | Matsumoto et al. |
| 2006/0045934 A1 | 3/2006 | Kabse et al. |
| 2006/0077241 A1 | 4/2006 | Silverbrook |
| 2006/0099287 A1 | 5/2006 | Kim et al. |
| 2006/0110443 A1 | 5/2006 | Payumo et al. |
| 2006/0111807 A1 | 5/2006 | Gothait et al. |
| 2006/0115433 A1 | 6/2006 | Andersen et al. |
| 2006/0127153 A1 | 6/2006 | Menchik et al. |
| 2006/0141145 A1 | 6/2006 | Davidson et al. |
| 2006/0147580 A1 | 7/2006 | Nissen et al. |
| 2006/0188465 A1 | 8/2006 | Perrier et al. |
| 2006/0230970 A1 | 10/2006 | Pimia et al. |
| 2006/0268044 A1 | 11/2006 | Silverbrook |
| 2006/0268057 A1 | 11/2006 | Silverbrook |
| 2007/0182782 A1 | 8/2007 | Silverbrook |
| 2007/0182799 A1 | 8/2007 | Silverbrook |
| 2007/0187508 A1 | 8/2007 | Takayama |
| 2007/0188549 A1 | 8/2007 | Silverbrook |
| 2007/0195150 A1 | 8/2007 | Silverbrook |
| 2007/0196474 A1 * | 8/2007 | Withiam ............. A61Q 11/00 424/465 |
| 2007/0252871 A1 | 11/2007 | Silverbrook |
| 2007/0259010 A1 | 11/2007 | Yoo et al. |
| 2007/0289705 A1 | 12/2007 | Johnson et al. |
| 2008/0042321 A1 | 2/2008 | Russell et al. |
| 2008/0062214 A1 | 3/2008 | Silverbrook |
| 2008/0068416 A1 | 3/2008 | Silverbrook |
| 2008/0105144 A1 | 5/2008 | Tetsuka et al. |
| 2008/0110395 A1 | 5/2008 | Kritchman et al. |
| 2008/0118655 A1 | 5/2008 | Kritchman |
| 2008/0121130 A1 | 5/2008 | Kritchman |
| 2008/0121172 A1 | 5/2008 | Kritchman et al. |
| 2008/0124464 A1 | 5/2008 | Kritchman et al. |
| 2008/0138515 A1 | 6/2008 | Williams |
| 2008/0180509 A1 | 7/2008 | Maki |
| 2008/0192074 A1 | 8/2008 | Dubois et al. |
| 2008/0211132 A1 | 9/2008 | Feenstra |
| 2008/0229961 A1 | 9/2008 | Schneider et al. |
| 2008/0231645 A1 | 9/2008 | Silverbrook |
| 2008/0241404 A1 | 10/2008 | Allaman et al. |
| 2008/0259434 A1 | 10/2008 | Nagayama |
| 2008/0269939 A1 | 10/2008 | Kritchman |
| 2008/0269940 A1 | 10/2008 | Silverbrook |
| 2008/0275181 A1 | 11/2008 | Win et al. |
| 2008/0277823 A1 | 11/2008 | Hayashi et al. |
| 2008/0281019 A1 | 11/2008 | Giller et al. |
| 2011/0028431 A1 | 2/2011 | Zerbe et al. |
| 2011/0070286 A1 | 3/2011 | Hugerth et al. |
| 2011/0097283 A1 | 4/2011 | Van Damme et al. |
| 2016/0015683 A1 | 1/2016 | McCarty |
| 2016/0158298 A1 | 6/2016 | Kolsky |
| 2016/0354310 A1 | 12/2016 | Bachmann et al. |
| 2017/0273902 A1 | 9/2017 | Bachmann et al. |
| 2017/0273903 A1 | 9/2017 | Bachmann et al. |
| 2017/0281539 A1 | 10/2017 | Bachmann et al. |
| 2017/0312261 A1 | 11/2017 | Changoer et al. |
| 2017/0368020 A1 | 12/2017 | Estey et al. |

FOREIGN PATENT DOCUMENTS

| | | |
|---|---|---|
| EP | 2609912 A1 | 7/2013 |
| WO | WO-9511007 A1 | 4/1995 |
| WO | WO-9534468 A1 | 12/1995 |
| WO | WO-9843762 A2 | 10/1998 |
| WO | WO-0026026 A1 | 5/2000 |
| WO | WO-02064109 A2 | 8/2002 |
| WO | WO-2004108398 A1 | 12/2004 |
| WO | WO-2006/010939 | 2/2006 |
| WO | WO-2006/050314 | 5/2006 |
| WO | WO-2009120080 A1 | 10/2009 |
| WO | WO-2016092539 A1 | 6/2016 |
| WO | WO-2017059859 A1 | 4/2017 |
| WO | 2017/223309 A1 | 12/2017 |

OTHER PUBLICATIONS

Abbadie, C. Chemokines, chemokine receptors and pain. Trends Immunol. Oct. 2005;26(10):529-34.

Cady et al., A double-blind placebo-controlled pilot study of sublingual feverfew and ginger (LipiGesic™ M) in the treatment of migraine. Headache. Jul.-Aug. 2011;51(7):1078-86.

Cady et al., Cocoa-enriched diets enhance expression of phosphatases and decrease expression of inflammatory molecules in trigeminal ganglion neurons. Brain Res. Apr. 6, 2010;1323:18-32.

Chang et al., Mammalian MAP kinase signalling cascades. Nature. Mar. 1, 2001;410(6824):37-40.

(56) References Cited

OTHER PUBLICATIONS

DeLeo et al., Neuroimmune activation and neuroinflammation in chronic pain and opioid tolerance/hyperalgesia. Neuroscientist. Feb. 2004;10(1):40-52.

Dickinson et al., Diverse physiological functions for dual-specificity MAP kinase phosphatases. J Cell Sci. Nov. 15, 2006;119(Pt 22):4607-15.

Gao et al., JNK-induced MCP-1 production in spinal cord astrocytes contributes to central sensitization and neuropathic pain. J Neurosci. Apr. 1, 2009;29(13):4096-108.

Inoue et al., SAD: a presynaptic kinase associated with synaptic vesicles and the active zone cytomatrix that regulates neurotransmitter release. Neuron. Apr. 20, 2006;50(2):261-75.

Ji et al., Central sensitization and LTP: do pain and memory share similar mechanisms? Trends Neurosci. Dec. 2003;26(12):696-705.

Ji et al., Possible role of spinal astrocytes in maintaining chronic pain sensitization: review of current evidence with focus on bFGF/JNK pathway. Neuron Glia Biol. Nov. 2006;2(4):259-69.

Ji, R. Mitogen-activated protein kinases as potential targets for pain killers. Curr Opin Investig Drugs. Jan. 2004;5(1):71-5.

Ji, R. Peripheral and central mechanisms of inflammatory pain, with emphasis on MAP kinases. Curr Drug Targets Inflamm Allergy. Sep. 2004;3(3):299-303.

Jin et al., P38 mitogen-activated protein kinase is activated after a spinal nerve ligation in spinal cord microglia and dorsal root ganglion neurons and contributes to the generation of neuropathic pain. J Neurosci. May 15, 2003;23(10):4017-22.

Julius et al., Molecular mechanisms of nociception. Nature. Sep. 13, 2001;413(6852):203-10.

Latremoliere et al., Central sensitization: a generator of pain hypersensitivity by central neural plasticity. J Pain. Sep. 2009;10(9):895-926.

McMahon et al., Current challenges in glia-pain biology. Neuron. Oct. 15, 2009;64(1):46-54.

Milligan et al., Pathological and protective roles of glia in chronic pain. Nat Rev Neurosci. Jan. 2009;10(1):23-36.

Romero-Sandoval et al., A comparison of spinal Iba1 and GFAP expression in rodent models of acute and chronic pain. Brain Res. Jul. 11, 2008;1219:116-26.

Scholz et al., The neuropathic pain triad: neurons, immune cells and glia. Nat Neurosci. Nov. 2007;10(11):1361-8.

Trang et al., P2X4-receptor-mediated synthesis and release of brain-derived neurotrophic factor in microglia is dependent on calcium and p38-mitogen-activated protein kinase activation. J Neurosci. Mar. 18, 2009;29(11):3518-28.

Turjanski et al., MAP kinases and the control of nuclear events. Oncogene. May 14, 2007;26(22):3240-53.

Wang et al., Regulation of innate immune response by MAP kinase phosphatase-1. Cell Signal. Jul. 2007;19(7):1372-82.

Watkins et al., Beyond neurons: evidence that immune and glial cells contribute to pathological pain states. Physiol Rev. Oct. 2002;82(4):981-1011.

White et al., Chemokines as pain mediators and modulators. Curr Opin Anaesthesiol. Oct. 2008;21(5):580-5.

Woolf et al., Neuronal plasticity: increasing the gain in pain. Science. Jun. 9, 2000;288(5472):1765-9.

Wu et al., Mice lacking MAP kinase phosphatase-1 have enhanced MAP kinase activity and resistance to diet-induced obesity. Cell Metab. Jul. 2006;4(1):61-73.

Zhuang et al., A peptide c-Jun N-terminal kinase (JNK) inhibitor blocks mechanical allodynia after spinal nerve ligation: respective roles of JNK activation in primary sensory neurons and spinal astrocytes for neuropathic pain development and maintenance. J Neurosci. Mar. 29, 2006;26(13):3551-60.

Bouaboula, et al., "Activation of Mitogen—Activated Protein Kinases by Stimulation of the Central Cannabinoid Receptor CB1," Biochemical Journal; 312(2):637-642, 1995.

CanChew Gum (Website Archive dated Sep. 11, 2015) (Accessed from https://web.archive.org/web/20150911073913/https://www.canchewgum.com/ 2 pages.

CanChew Gum FAQ (Website Archive dated Sep. 27, 2015) Accessed from https://web.archive.org/web/20150927212115/https://www.canchewgum.com/faqs.html, 2 pages.

CanChew Biotechnologies CBD-Infused Chewing Gum (https://www.medicaljane.com/2013/08/30/canchew-biotechnologies-cbd-infused-chewing-gum/ 4 pages.

Cannabis Market, World Drug Report 2007, 95-121.

Chaudhary et al. (2012) "Directly Compressible Medicated Chewing Gum Formulation for Quick Relief from Common Cold", International journal of pharmaceutical investigation, 2(3):123-133.

Devinsky et al. (Jun. 2014) "Cannabidiol: Pharmacology and Potential Therapeutic Role in Epilepsy and Other Neuropsychiatric Disorders", Epilepsia, 55(6):23 pages.

Jacobsen et al. (Jun. 2004) "Medicated Chewing Gum Pros and Cons", American Journal of Drug Delivery, 2(2):75-88.

Reichard (Aug. 30, 2013) "CanChew Biotechnologies CBD-Infused Chewing Gum", Available at <https://www.medicaljane.com/2013/08/30/canchew-biotechnologies-cbd-infused-chewing-gum/>, 03 pages.

Siddique (Jun. 2, 2012) "Pakistan's Goat-Grown Hashish", Radio Free Europe, Radio Liberty, 04 pages.

Sigma-Aldrich (Nov. 12, 2014) "Particle Size Conversion Table", Available at <https://www.sigmaaldrich.com/chemistry/stockroom-reagents/learning-center/technical-library/particle-size-conversion.html>, retrieved on Nov. 12, 2014, 01 page.

Vranikova et al. (2013) "Liquisolid Systems and Aspects Influencing their Research and Development", Acta Pharmaceutica, 63(4):447-465.

Welti-Chanes et al. (2008) "Phase Transitions and Hygroscopicity in Chewing Gum Manufacture", Food Engineering: Integrated Approaches, 139-153.

Wikipedia (2019) "Sugar substitute", Accessed on https://en.wikipedia.org/wiki/Sugar, 15 pages.

Zhang et al. (2002) "Oral Mucosal Drug Delivery", Clinical pharmacokinetics, 41(9):661-680.

\* cited by examiner

Neuronal Staining of Upper Spinal Cord

Blue = DAPI (nucleus of all cells)

Neuronal Staining of Trigeminal Ganglion
Blue = DAPI (nucleus of all cells)

ORAL COMPOSITIONS DELIVERING THERAPEUTICALLY EFFECTIVE AMOUNTS OF CANNABINOIDS

CROSS REFERENCE TO RELATED APPLICATIONS

This application is a U.S. Divisional Application of U.S. application Ser. No. 15/615,521, filed Jun. 6, 2017, now U.S. Pat. No. 10,765,658, which claims the benefit of and priority to U.S. Provisional Application No. 62/353,420, filed on Jun. 22, 2016. The entire contents of which are-incorporated herein by reference.

FIELD OF THE INVENTION

Embodiments of the invention are directed to oral compositions for the delivery of cannabinoids to a subject.

BACKGROUND

Neuronal-glial interactions are implicated in normal information processing, neuroprotection, and modulation of neuronal activity including rate of spontaneous firing and threshold of activation. It is generally believed that inflammatory and neuropathic pain are an expression of neural plasticity, which can occur as both peripheral sensitization, an increase in the sensitivity and excitability of primary sensory neurons in the peripheral nervous system (PNS), and central sensitization, an increase in the activity and excitability of nociceptive neurons in the spinal cord and brain in the central nervous system (CNS) that leads to the development and maintenance of chronic pain (Ji et al., *Trends in Neurosciences.* 26(12):696-705 (2003); Julius D. & Basbaum A. I., *Nature. September* 13; 413(6852):203-10 (2001); Woolf C. J. & Salter M. W., Science. 2000 Jun. 9; 288(5472):1765-9; Latremoliere A. & Woolf C. J. *The Journal of Pain.* 2009 September; 10(9):895-926). In recent years, it is increasingly recognized that glial cells in the PNS (e.g., Schwann cells and satellite cells) and CNS (e.g., astrocytes and microglia) play a critical role in chronic pain processing by modulating neuronal excitability (Ji et al., *Neuron Glia Biology.* 2006 November; 2(4):259-69; McMahon S B & Malcangio M., *Neuron.* 2009 Oct. 15; 64(1):46-54; Milligan E D & Watkins L R, *Nature Reviews Neuroscience.* 2009 January; 10(1):23-36; Romero-Sandoval A et al., *Brain Research.* 2008 Jul. 11; 1219: 116-126; Scholz J & Woolf C J. *Nat Neuroscience.* 2007 November; 10(11): 1361-8). Nerve injury or activation of sensory neurons in response to inflammatory stimuli induces substantial changes in both microglia and astrocytes in the spinal cord (DeLeo J A et al., *Neuroscientist.* 2004 February; 10(1):40-52; Jin S X et al., *Journal of Neuroscience.* 2003 May 15; 23(10):4017-22; Zhuang Z Y et al., *Journal of Neuroscience.* 2006 Mar. 29; 26(13):3551-60). Furthermore, data from studies of glial inhibition support an important role of spinal microglia and astrocytes in enhancing inflammatory and neuropathic pain. It is generally believed that spinal glial cells enhance and maintain inflammatory and neuropathic pain by releasing potent neuromodulators, such as proinflammatory cytokines, chemokines, and growth factors (Abbadie C. *Trends in Immunology.* 2005 October; 26(10):529-34; Abbadie C. et al., *Brain Research Reviews.* 2009 April; 60(1):125-34; Gao Y J et al., *Journal of Neuroscience.* 2009 Apr. 1; 29(13):4096-108; Inoue E. et al., *Neuron.* 2006 Apr. 20; 50(2):261-75; Milligan E D & Watkins L R, *Nature Reviews Neuroscience.* 2009 January; 10(1):23-36; Trang T. et al., *Journal of Neuroscience.* 2009 Mar. 18; 29(11):3518-28; Watkins L R & Maier S F. *Physiological Reviews.* 2002 October; 82(4):981-1011; White F A & Wilson N M, *Current Opinion in Anesthesiology.* 2008 October; 21(5):580-5)).

SUMMARY

Embodiments are directed to oral compositions which deliver therapeutically effective amounts of cannabinoids to a subject in need thereof. In particular, the oral compositions comprise chewing gum, lozenges and fast-dissolving lozenges.

Other aspects are described infra.

BRIEF DESCRIPTION OF THE DRAWINGS

The patent or application contains at least one drawing executed in color. Copies of this patent or patent application publication with color drawing(s) will be provided by the Office upon request and payment of the necessary fee.

FIGS. 7 and 8 show the brain stains obtained for MKP-1 at 2 (FIG. 7) and 24 hours (FIG. 8) post-injection.

FIGS. 9 and 10 show the brains stains obtained for MKP-2 at 2 (FIG. 9) and 24 hours (FIG. 10) post-injection.

FIGS. 11 and 12 show the brain stains obtained for MKP-3 at 2 (FIG. 11) and 24 hours (FIG. 12) post-injection.

FIGS. 14, 15 and 16 show the upper spinal cord stains obtained for MKP-1 (FIG. 14), MKP-2 (FIG. 15) and MKP-3 (FIG. 16) at 2 hours post-injection.

FIGS. 17, 18 and 19 show the upper spinal cord stains obtained for MKP-1 (FIG. 17), MKP-2 (FIG. 18) and MKP-3 (FIG. 19) at 24 hours post-injection.

FIGS. 20, 21 and 22 show the upper spinal cord stains obtained for MKP-1 (FIG. 20), MKP-2 (FIG. 21) and MKP-3 (FIG. 22) at 48 hours post-injection.

FIGS. 24 and 25 show the staining of the trigeminal ganglion for MKP-1 (FIG. 24) and for MKP-2 (FIG. 25) at 24 hours post-injection.

FIGS. 26, 27 and 28 show the staining of the trigeminal ganglion for MKP-3 at 2 hours (FIG. 26), 24 hours (FIG. 27) and 48 hours (FIG. 28) post-injection.

FIGS. 29, 30 and 31 show the staining of the dorsal root ganglion for MKP-1 (FIG. 29), MKP-2 (FIG. 30) and MKP-3 (FIG. 31) at 24 hours post injection.

FIG. 32 shows the staining of the dorsal root ganglion for MKP-3 at 48 hours post-injection.

DETAILED DESCRIPTION

Figure 1:
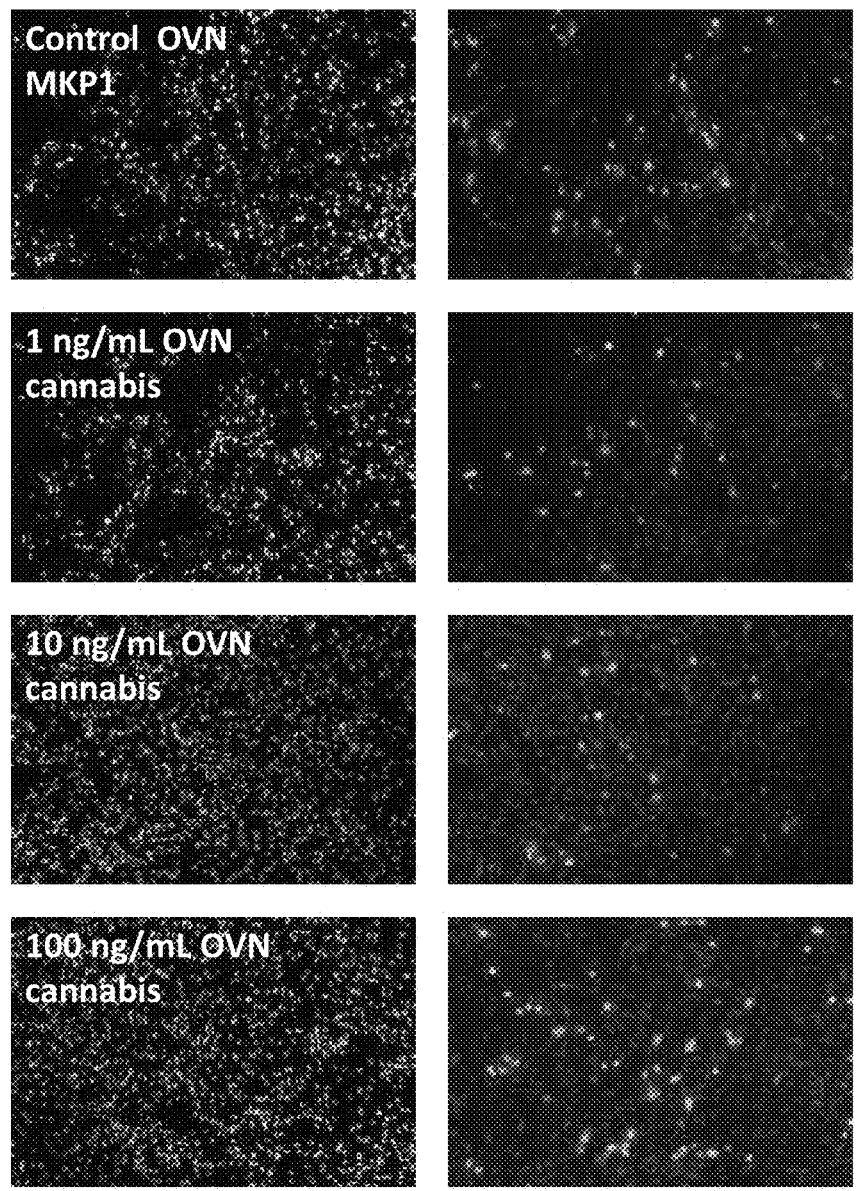
FIG. 1 is a series of representative images of trigeminal ganglia cultures that show cannabis stimulation of MKP1 in a concentration-dependent manner. Trigeminal neurons and glial cells were treated overnight with different concentrations of cannabis and the expression of MKP1 determined using immunocytochemistry (right panels). There is an increase in the expression and number of neurons (larger cells) and glial cells (smaller cells) in cultures treated with 10 or 100 ng/ml when compared to untreated control cultures. The same images on the right were co-stained with the nuclear dye DAPI to identify all cell in the cultures.
Figure 2:
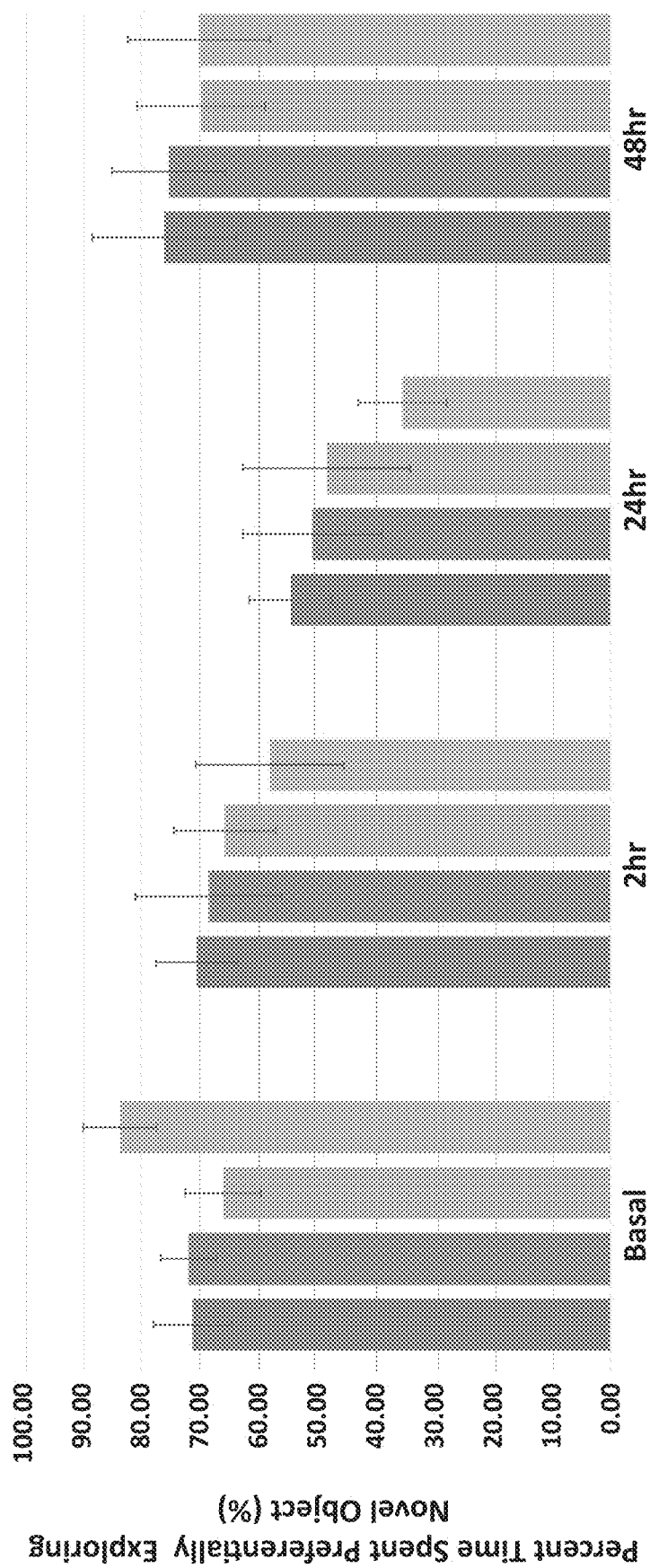
FIG. 2 shows the results obtained from the novel object recognition test based on the percent time a test animal preferentially spends exploring the novel object. The test animals were injected with 1 mg/kg Cannabis (n=7) or 0.1 mg/kg Cannabis (n=7) and the tests were conducted at 2 hr, 24 hr and 48 hr post-injection.
Figure 3:
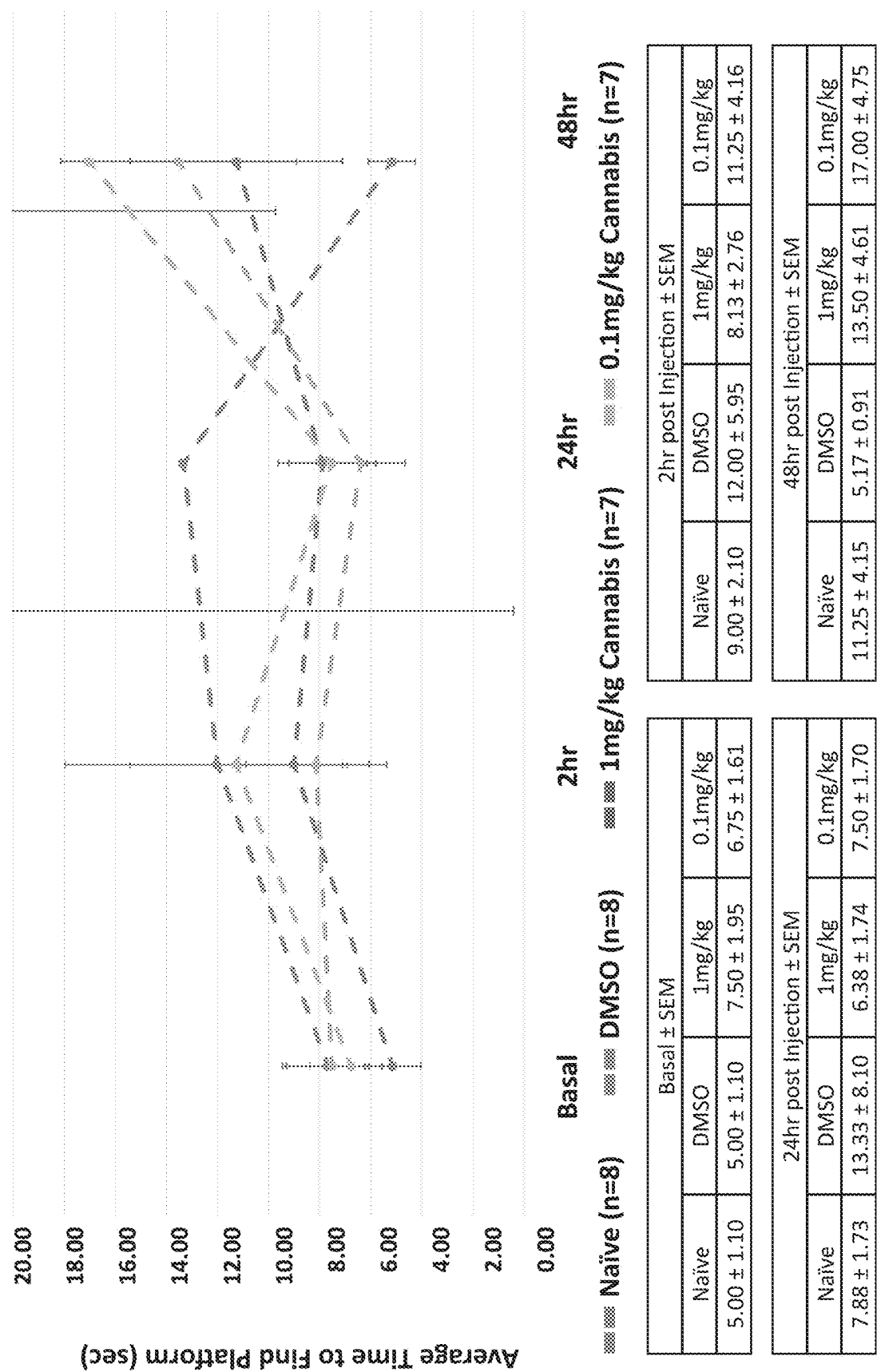
FIG. 3 shows the results from the Morris water maze test. The results are plotted as the average time the test animal takes to find the platform. The test animals were injected with 1 mg/kg Cannabis (n=7) or 0.1 mg/kg Cannabis (n=7) and the tests were conducted at 2 hr, 24 hr and 48 hr post-injection.
Figure 4:
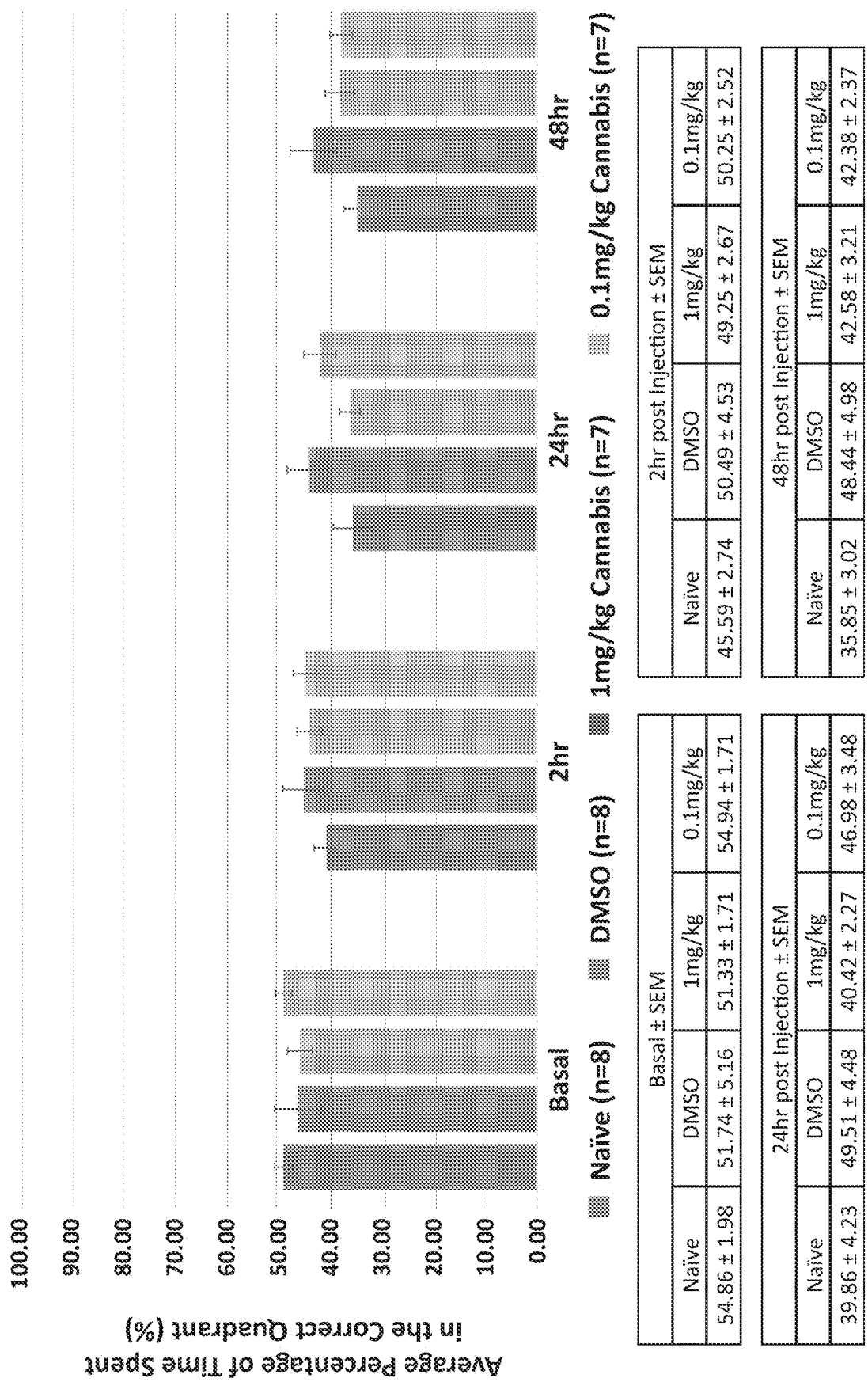
FIG. 4 shows the results from the Morris water maze probe test. The results are plotted as the average percentage time the test animal spends in the correct quadrant. The test animals were injected with 1 mg/kg Cannabis (n=7) or 0.1 mg/kg Cannabis (n=7) and the tests were conducted at 2 hr, 24 hr and 48 hr post-injection.
Figure 5:
FIG. 5 shows images from the nuclear staining of rat brain.
Figure 5:
Figure 6:
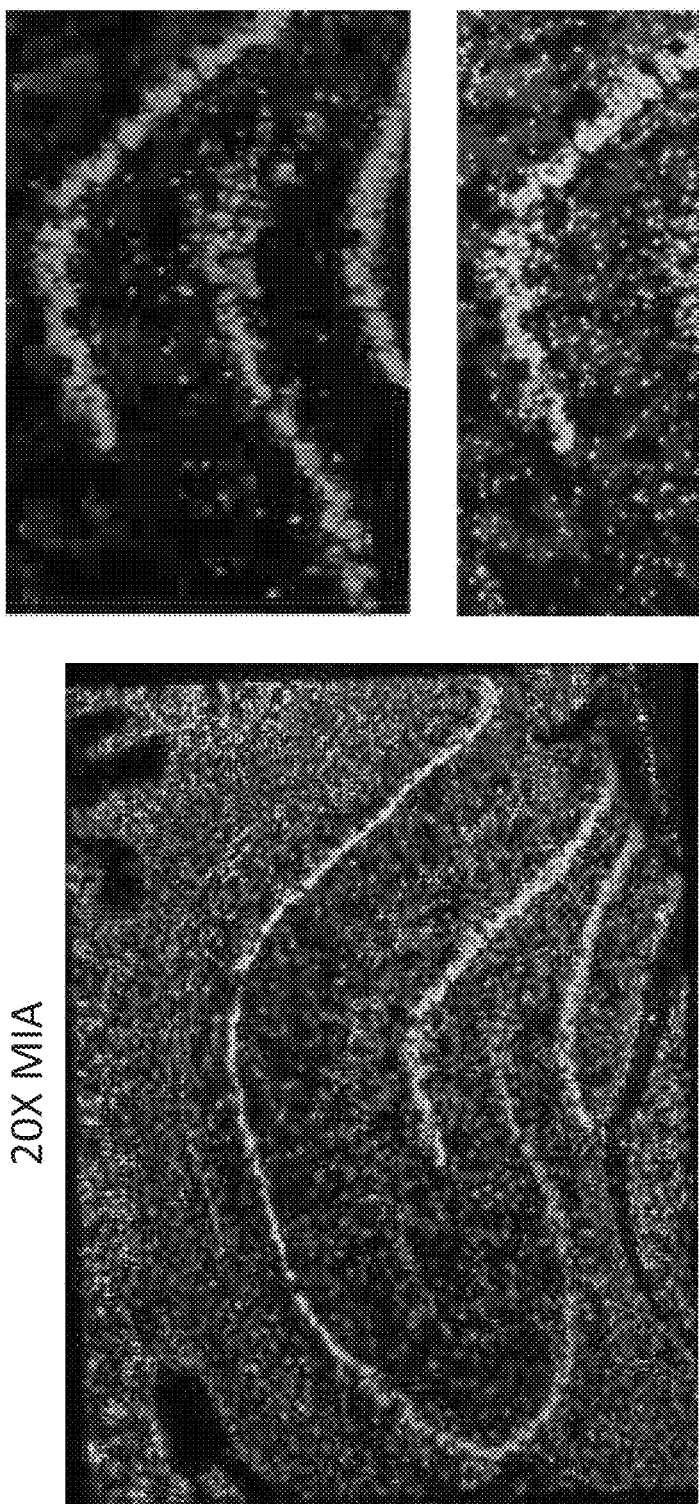
FIG. 6 shows images from the neuronal staining of the hippocampus.
Figure 7:
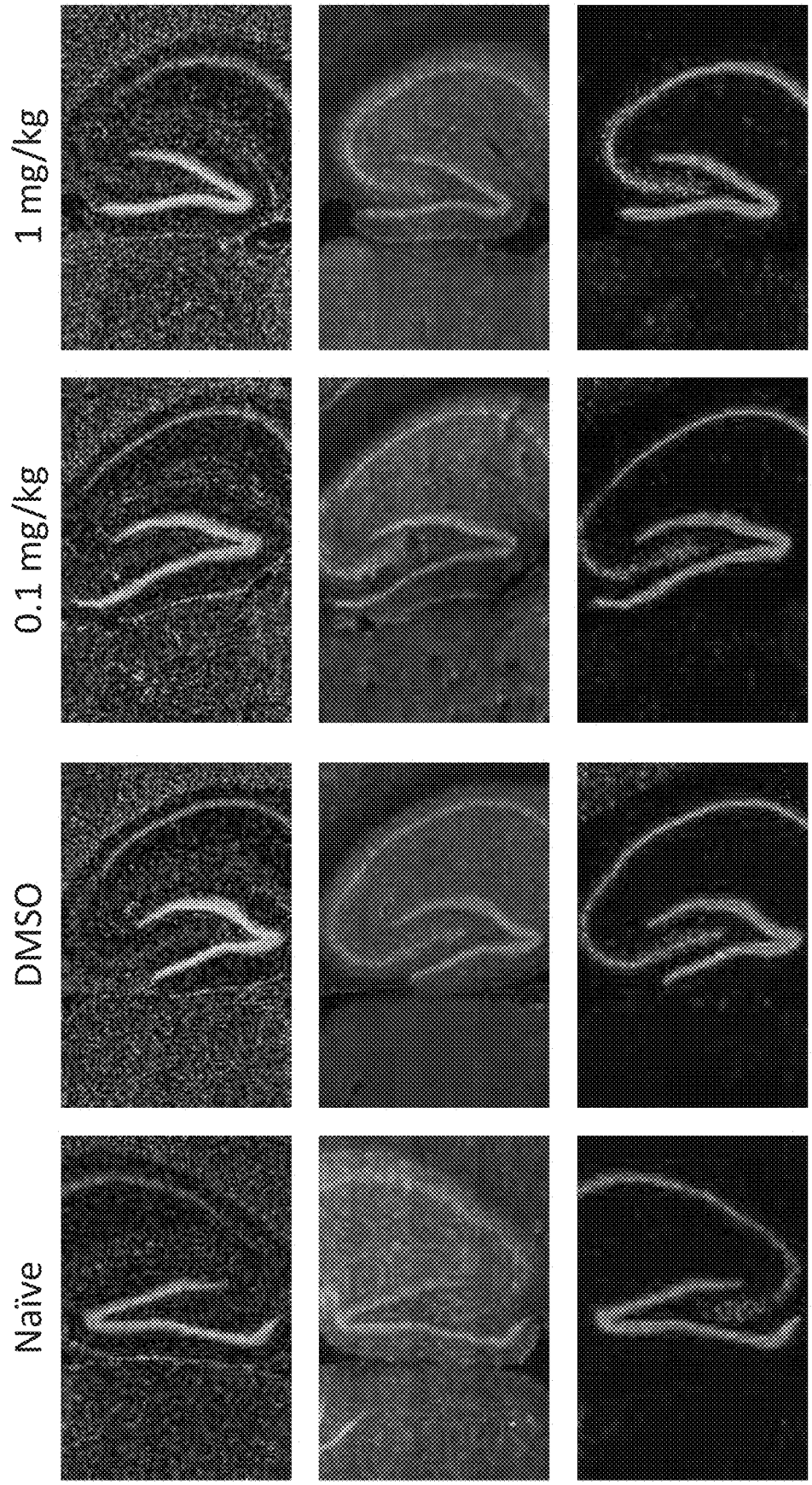
FIGS. 7-12, 14-22 and 24-32 are representative images for each of the experimental conditions to illustrate the cellular effect of cannabis on MKP levels in the brain, spinal cord, and ganglia obtained from naïve untreated animals, animals treated with vehicle solution, and animals administered either 1 mg/kg or 0.1 mg/kg cannabis.
Figure 8:
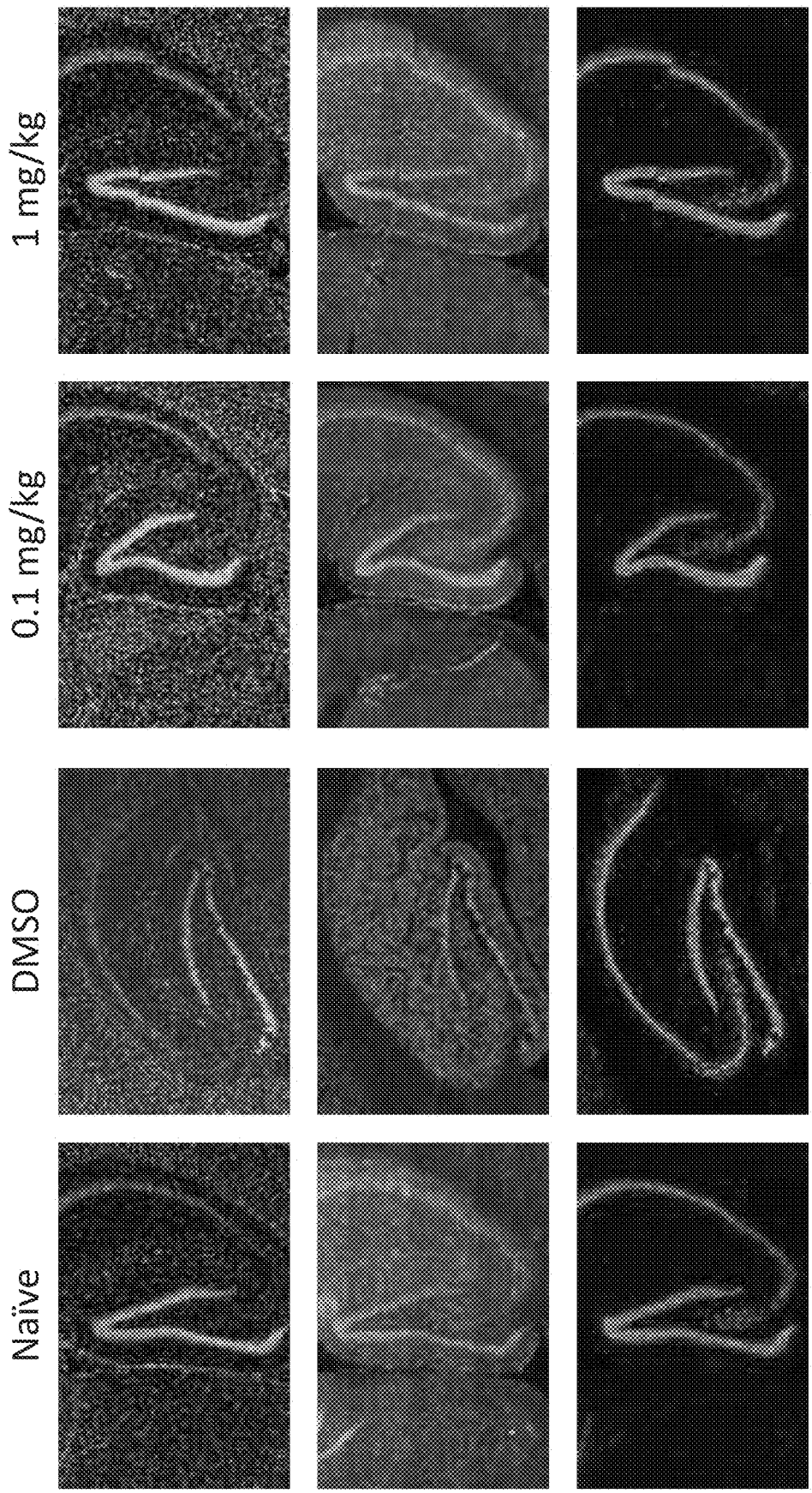
Figure 9:
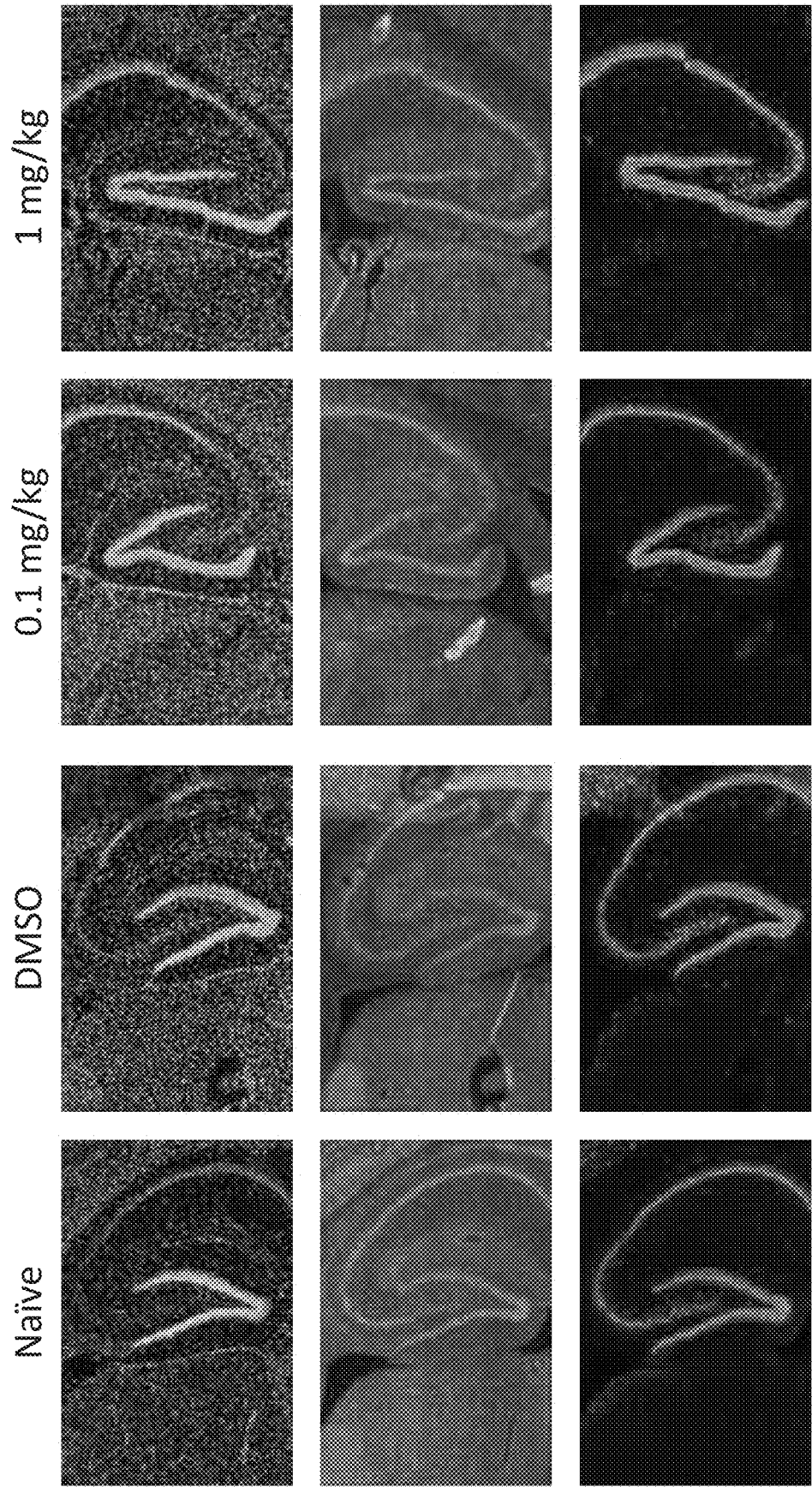
Figure 10:
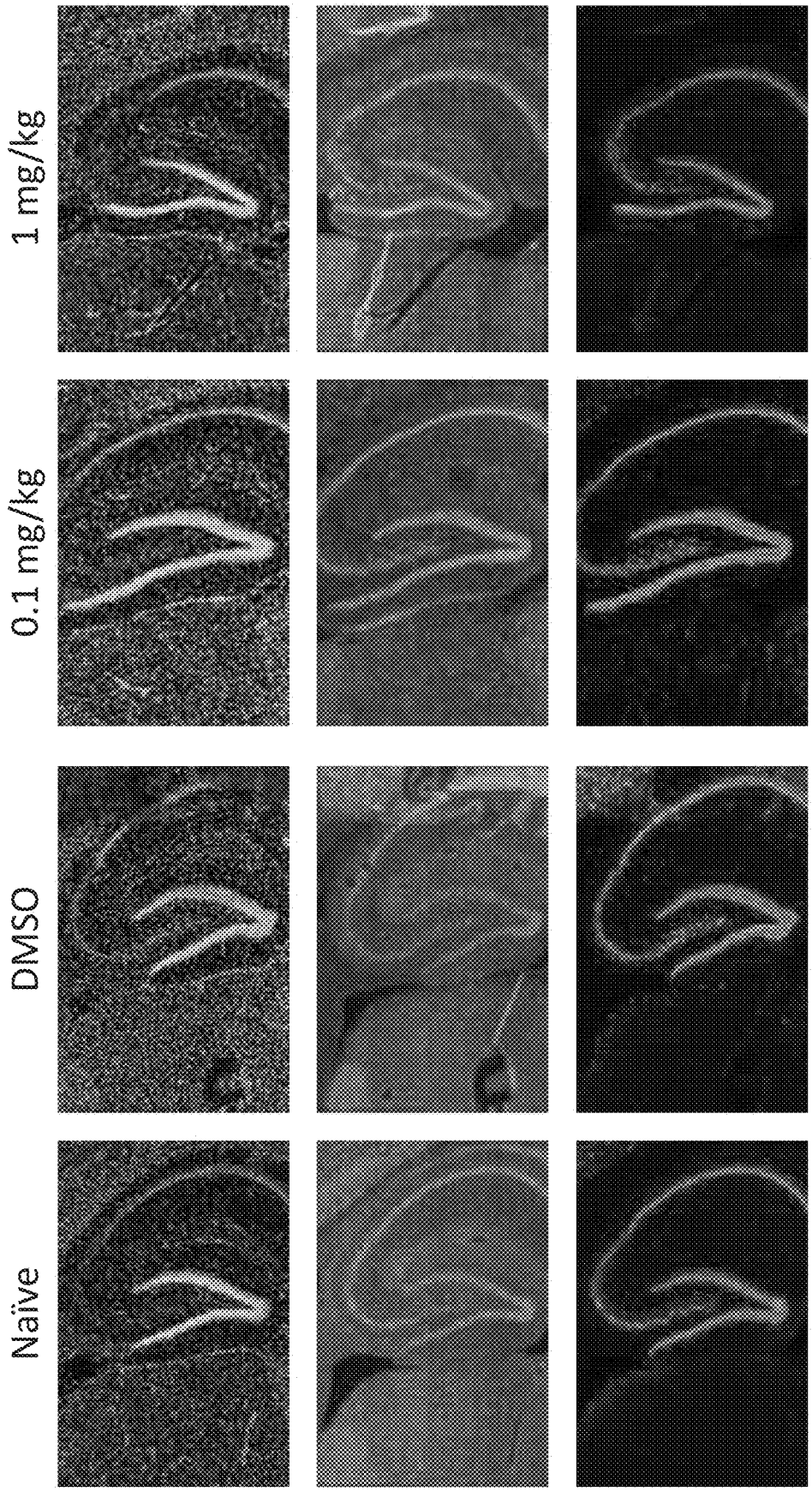
Figure 11:
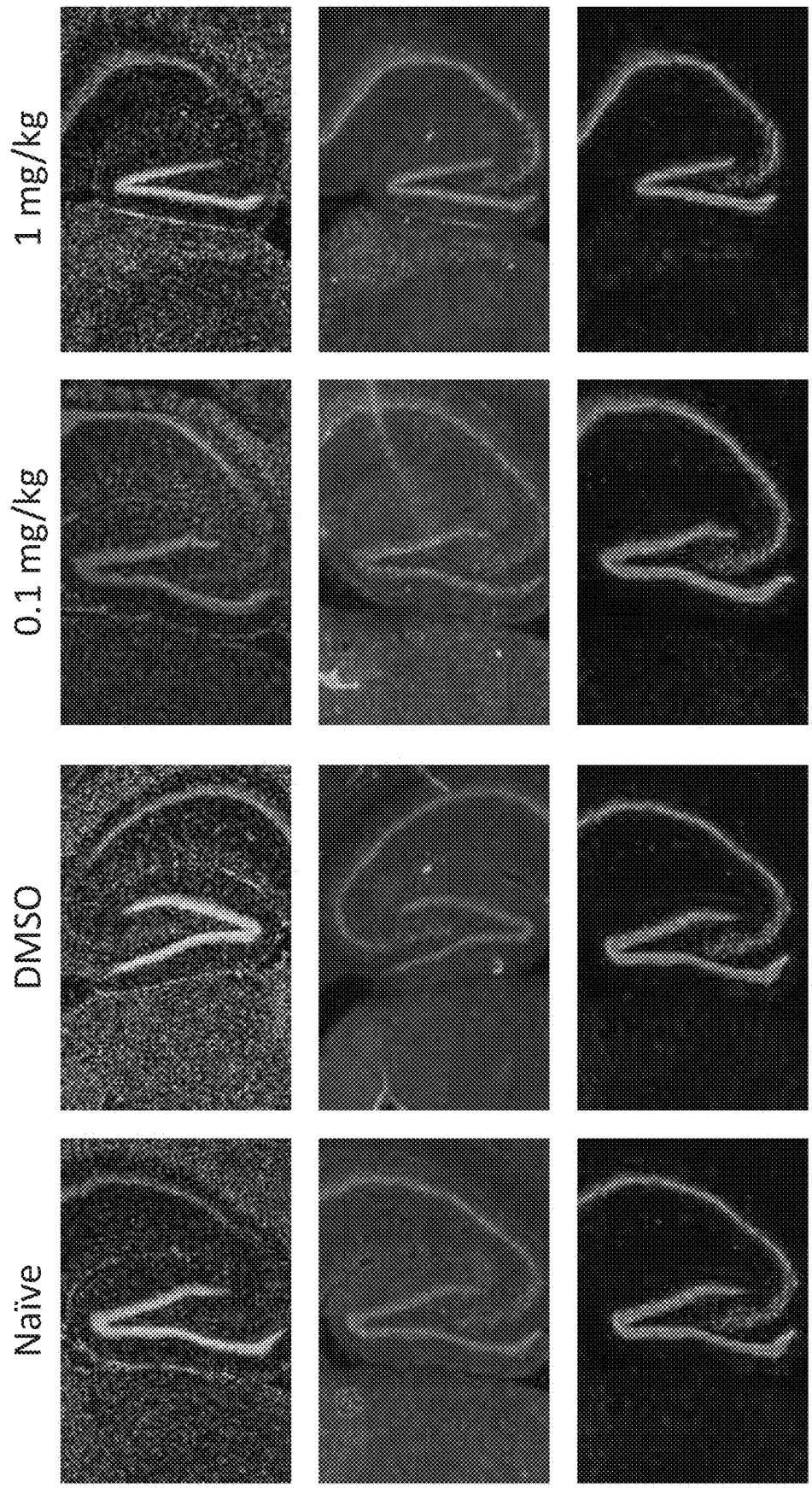
Figure 12:
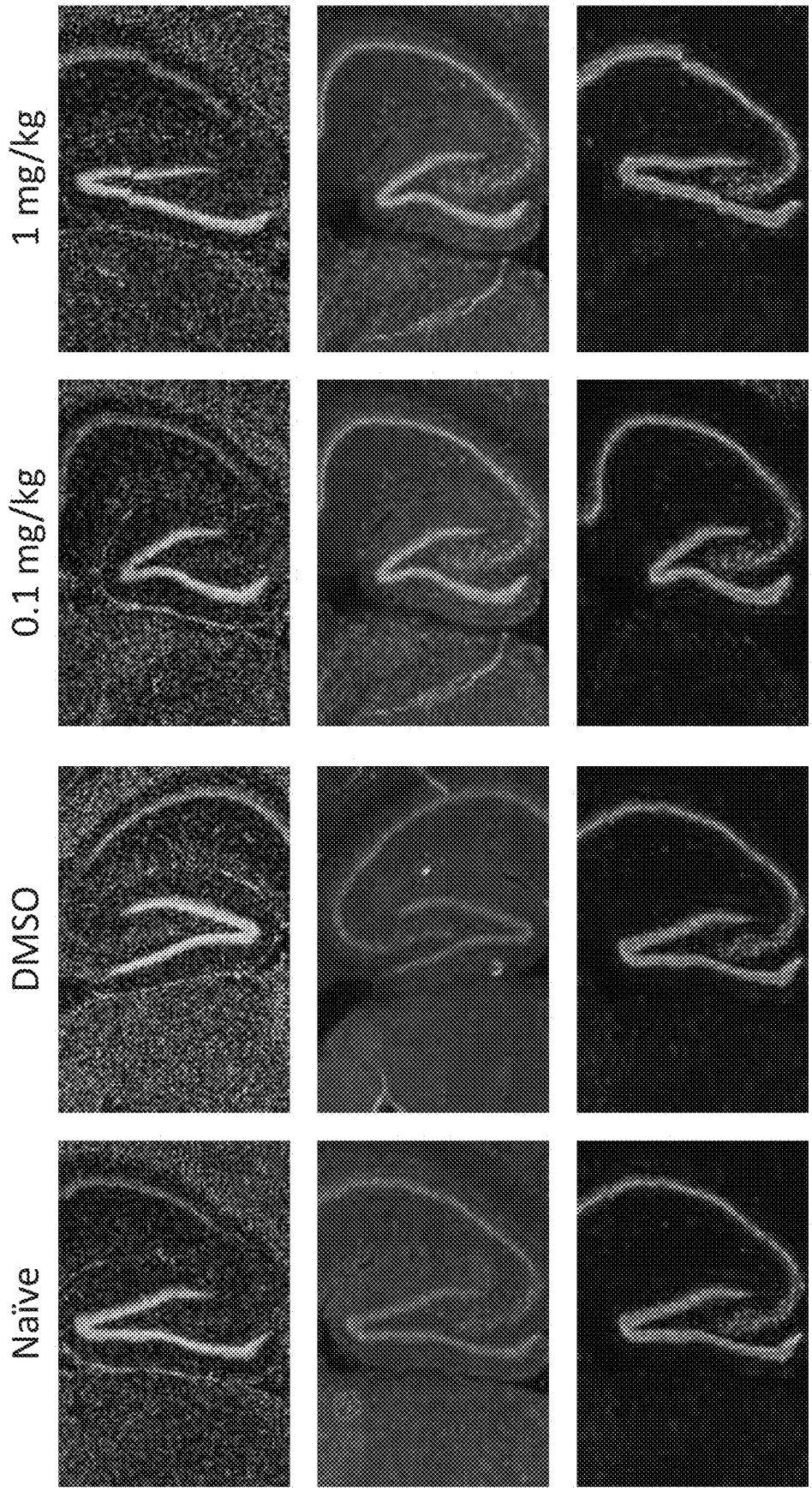
Figure 13:
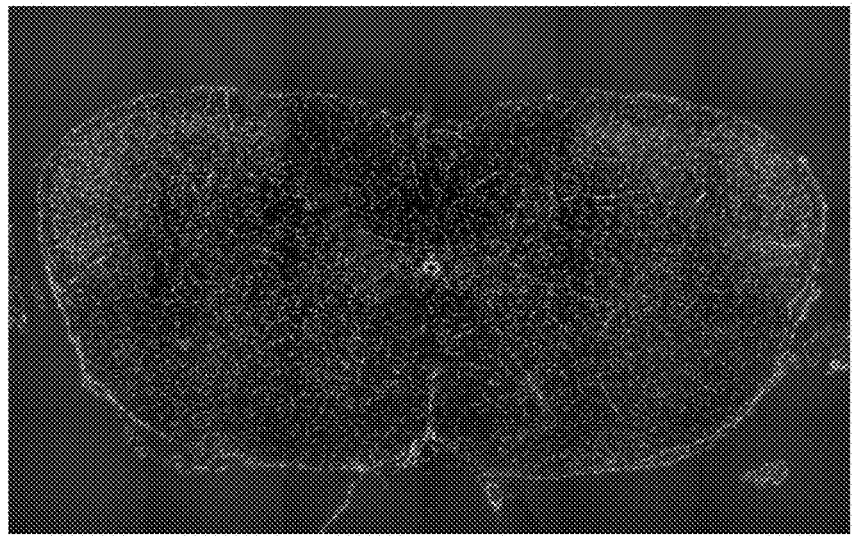
FIG. 13 shows the neuronal staining of the upper spinal cord.
Figure 13:
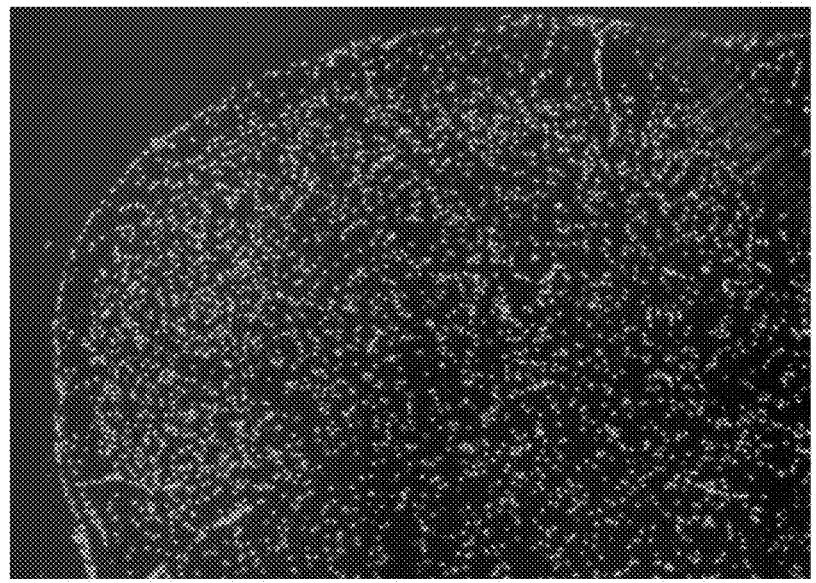
Figure 14:
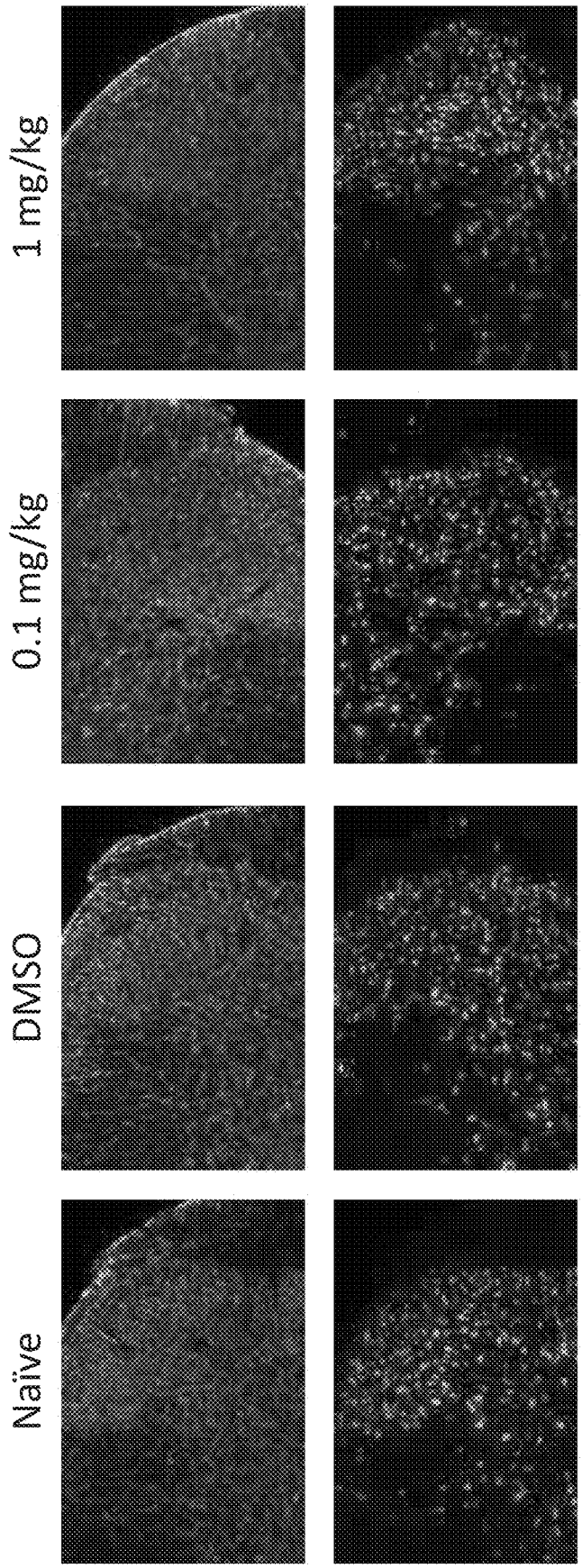
Figure 15:
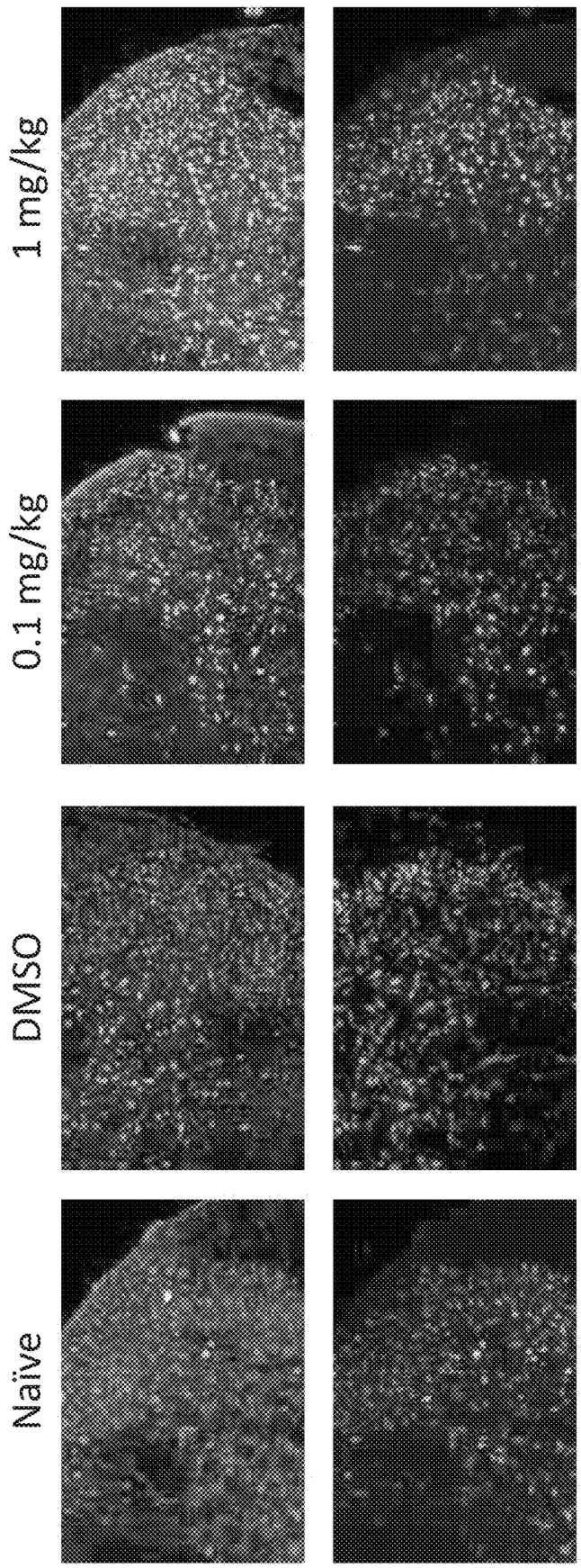
Figure 16:
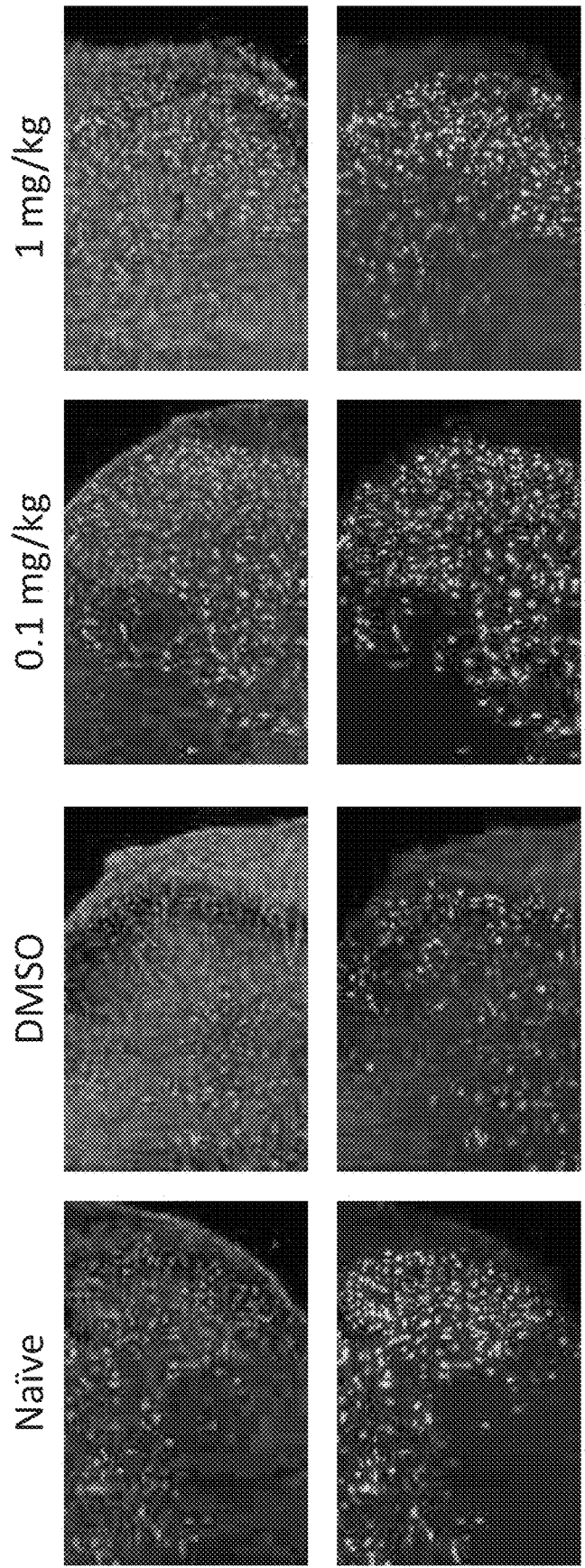
Figure 17:
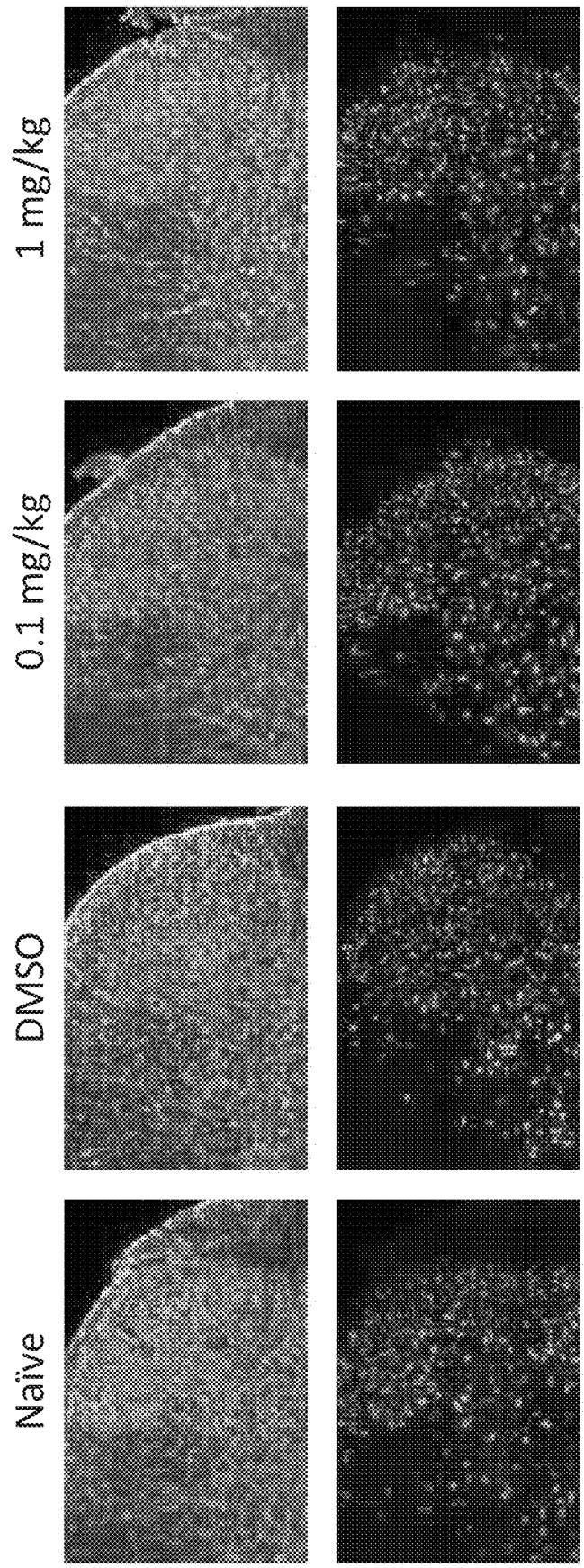
Figure 18:
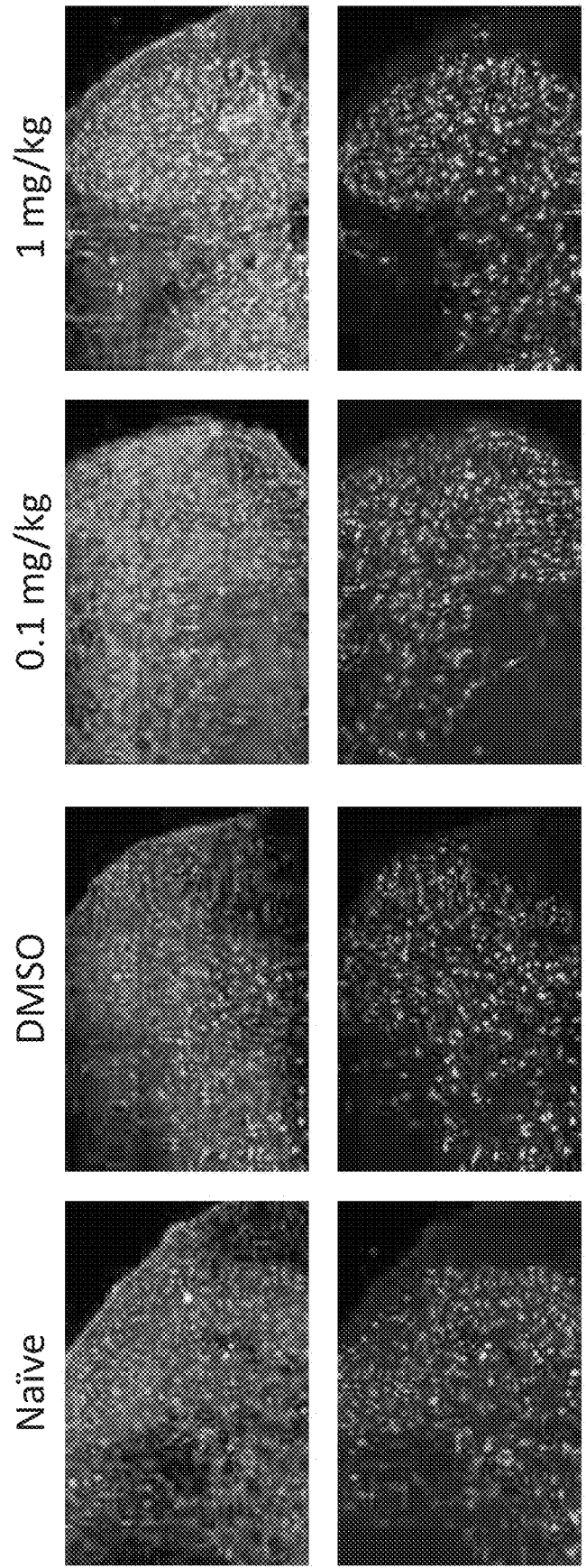
Figure 19:
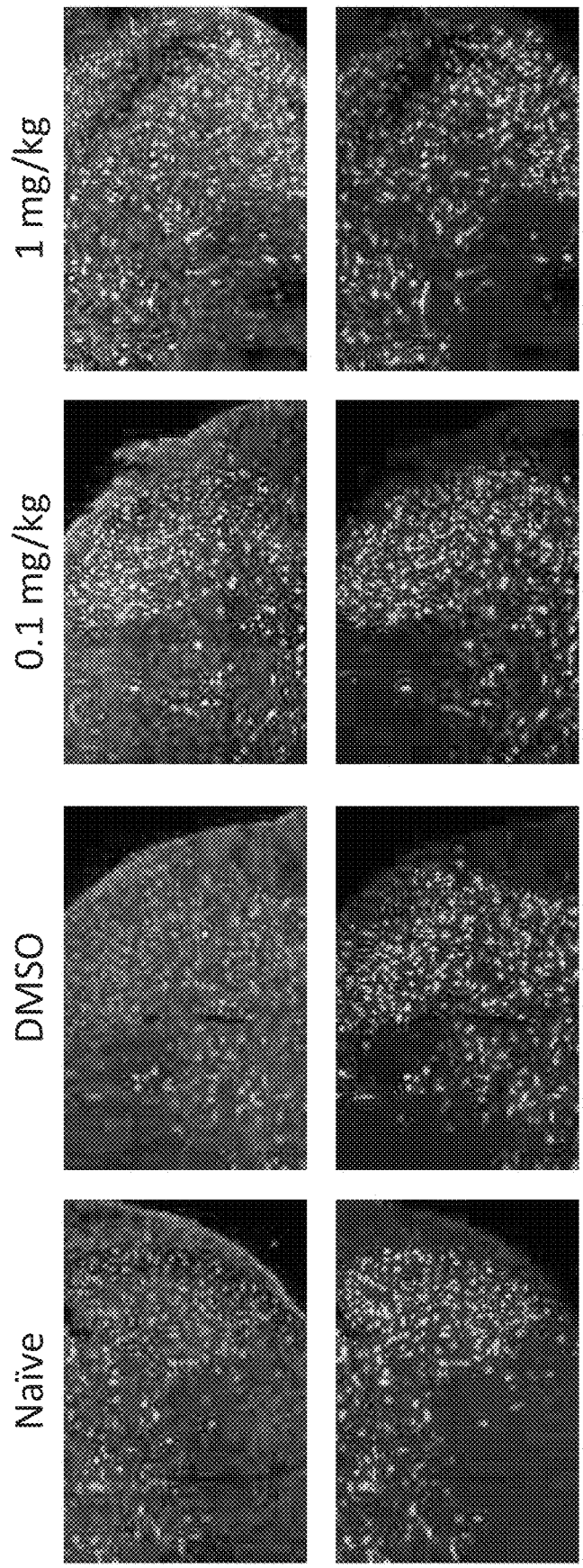
Figure 20:
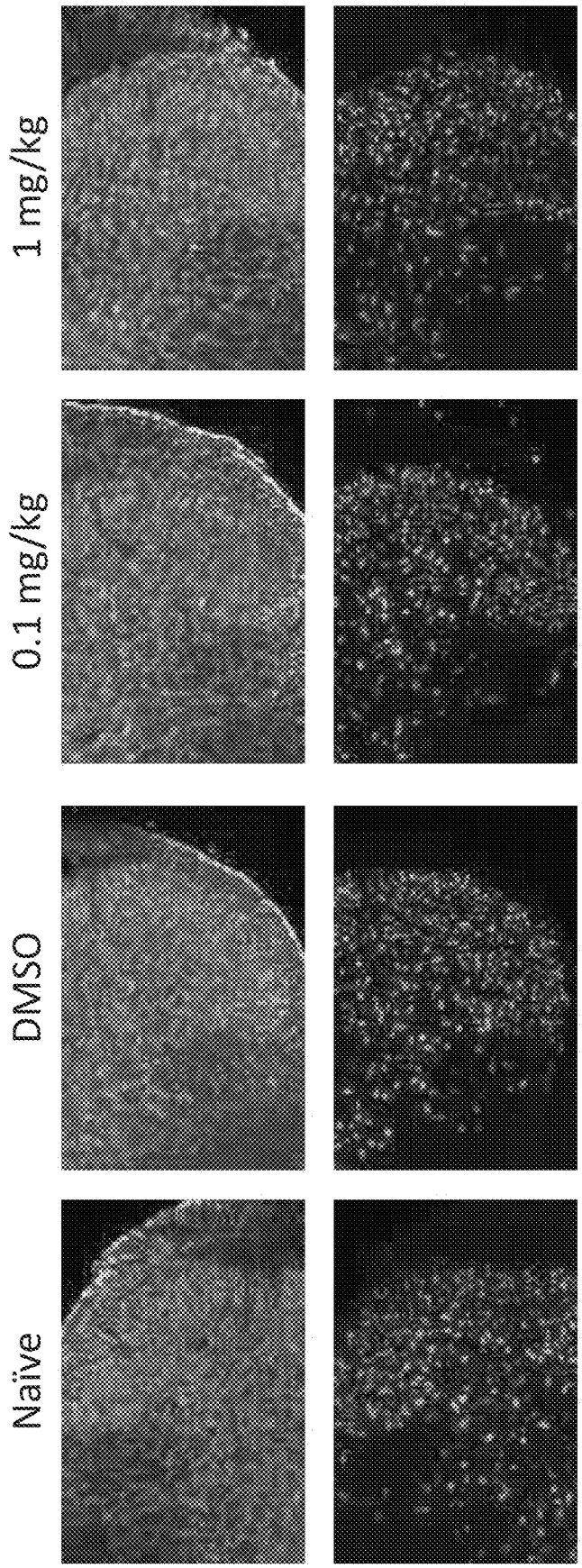
Figure 21:
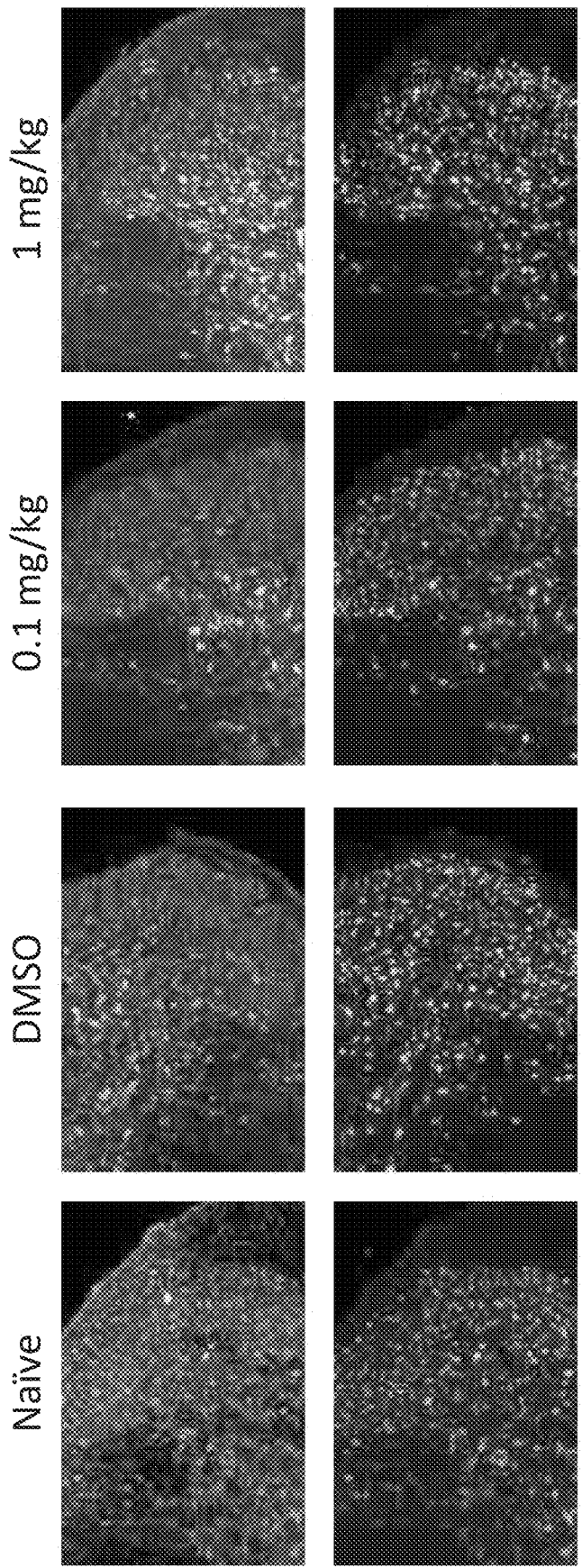
Figure 22:
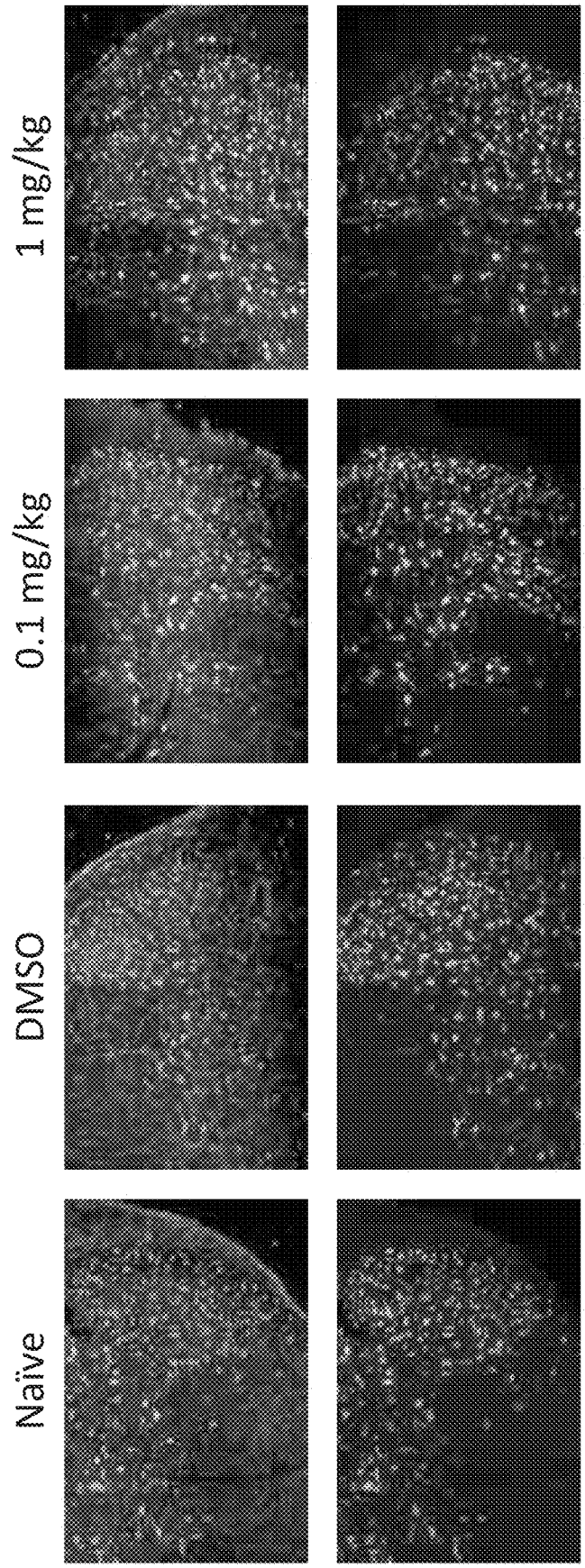
Figure 23:
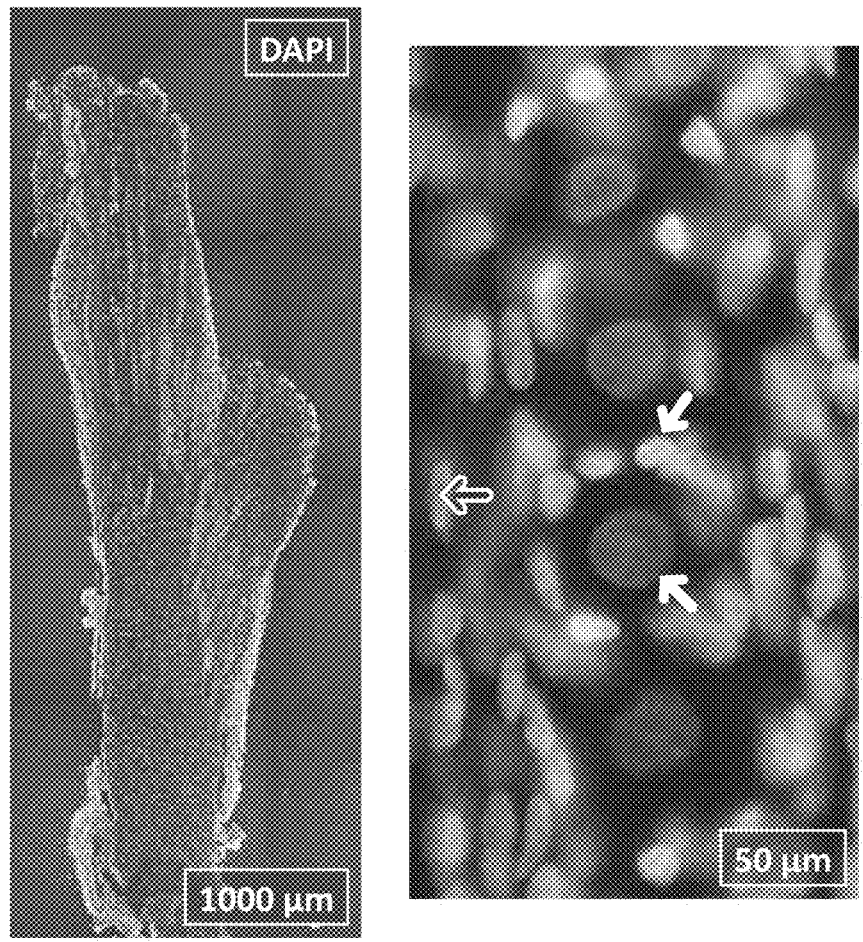
FIG. 23 shows the neuronal staining of the trigeminal ganglion.
Figure 24:
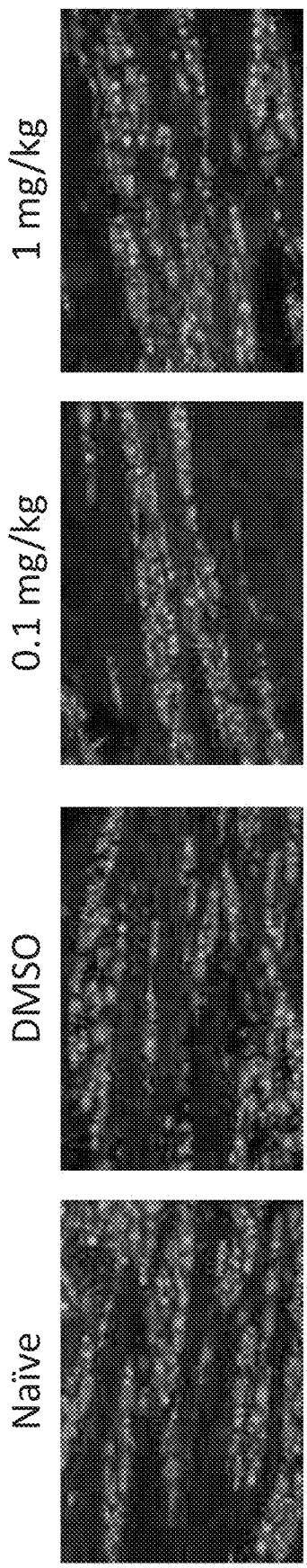
Figure 25:
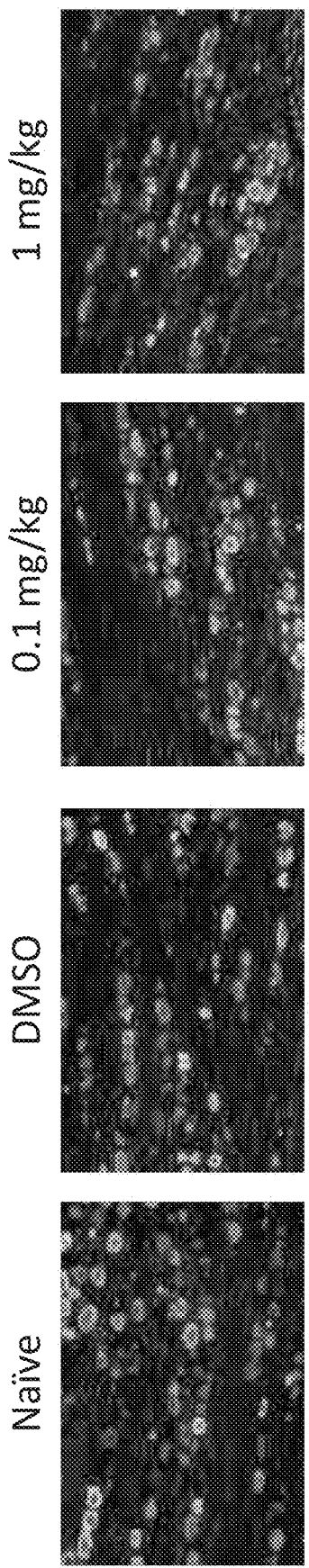
Figure 26:
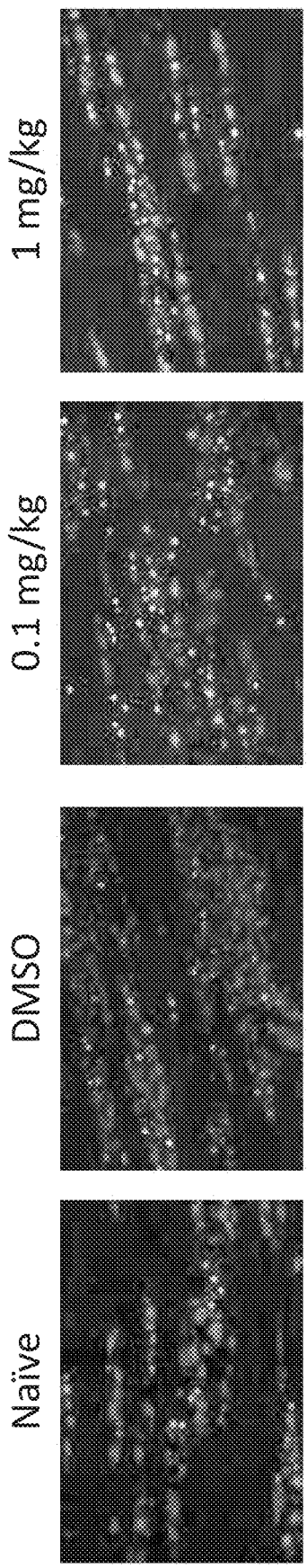
Figure 27:
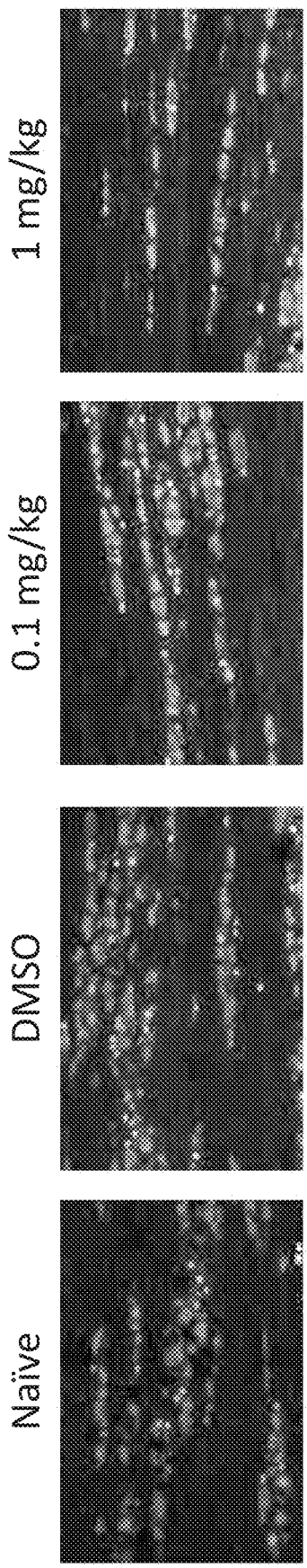
Figure 28:
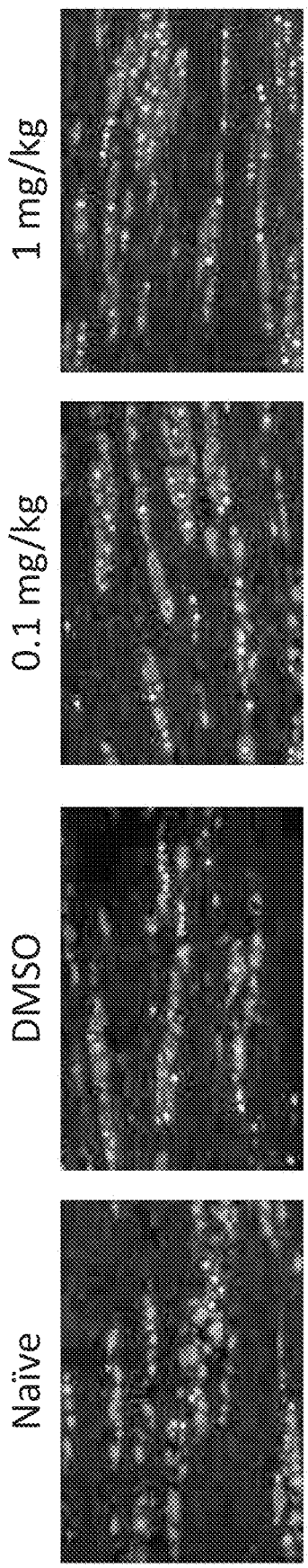
Figure 29:
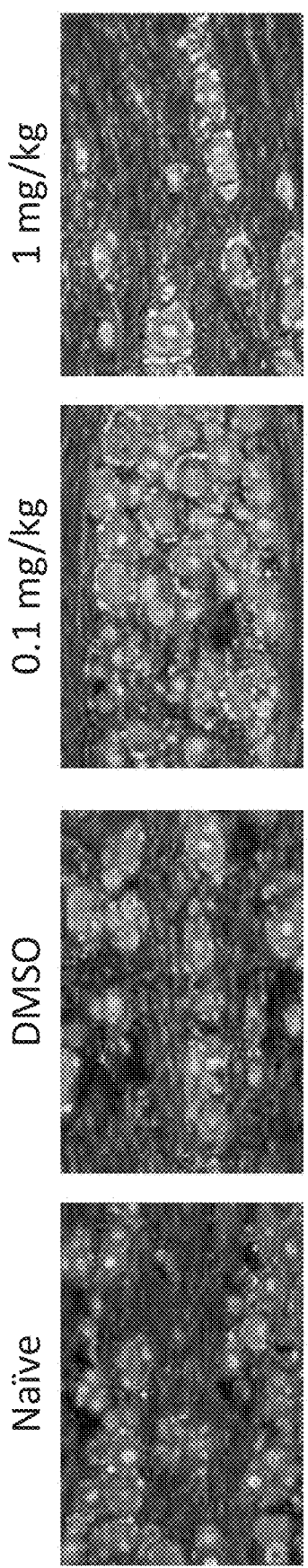
Figure 30:
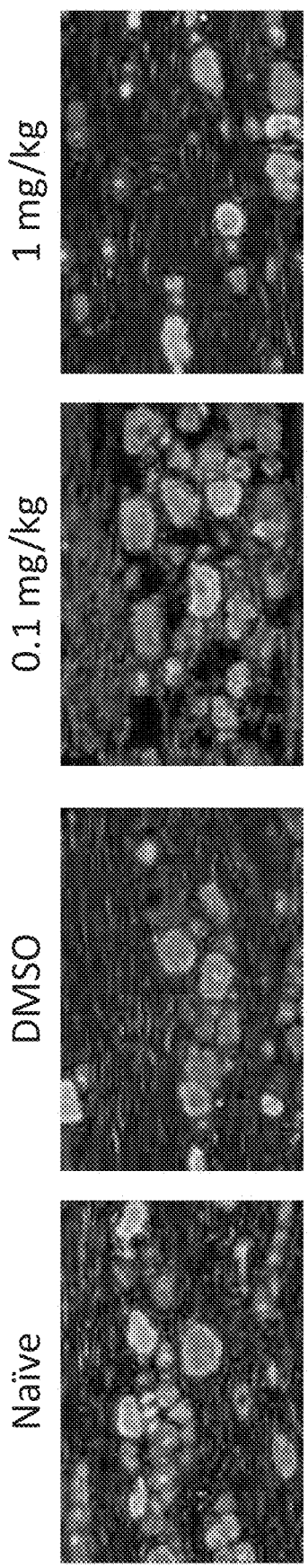
Figure 31:
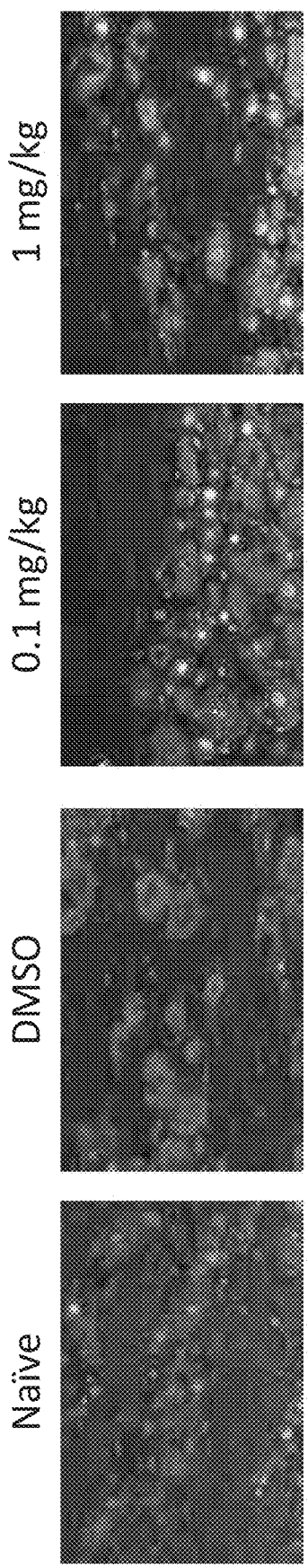
Figure 32:
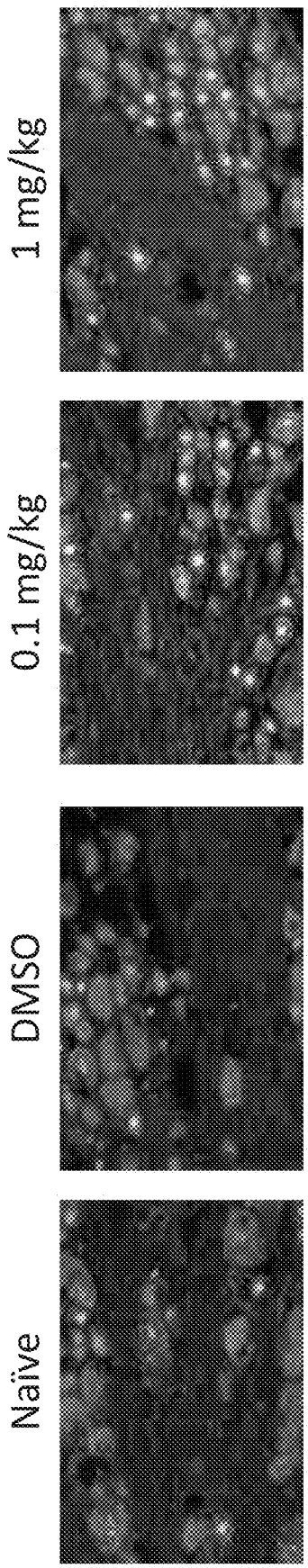

Many of the agents implicated in the initiation or maintenance of acute and chronic pain have been shown to directly activate the cellular signaling cascades collectively known as the mitogen-activated protein (MAP) kinase pathways (Ji, R R. *Current Opinion in Investigational Drugs.* 2004 January; 5(1):71-5; Ji, R R. Current Drug Targets Inflammation & Allergy. 2004 September; 3(3):299-303). There are four distinct groups of MAP kinases present in mammalian cells: extracellular signal-regulated kinase (ERK1/2); Jun amino-terminal kinase (JNK 1/2/3); p38 proteins (p38 α/β/γ), and ERKS (Chang L. & Karin, M. *Nature.* 2001 Mar. 1; 410(6824):37-40). MAPK are activated by phosphorylation in response to a variety of inflammatory stimuli including cytokines, ceramides, and nitric oxide. Upon activation, these pathways are responsible for controlling many cellular functions, including inflammation, proliferation, differentiation, migration, and apoptosis (Turjanski A G et al. *Oncogene.* 2007 May 14; 26(22):3240-53).

Furthermore, over-expression of MAP kinase pathways has been reported to facilitate inflammation and nociception, and even tissue damage (Ji, R R. *Current Opinion in Investigational Drugs.* 2004 January; 5(1):71-5). Importantly, MAP kinases play a pivotal role in the underlying pathology of multiple orofacial diseases by facilitating increased synthesis of cytokines such as IL-1β and IL-6 that promote and sustain inflammatory and neuropathic pain.

The duration and magnitude of the MAP kinase response is controlled by MAP kinase phosphatases (MKP), which are enzymes involved in restoring elevated kinase levels to normal via dephosphorylation of MAP kinases (Dickinson R J & Keyse S M. *Journal of Cell Science.* 2006 Nov. 15; 119(Pt 22):4607-15). There are 11 known MKPs that are expressed in a variety of different cell types including neurons and glia (Wu J J, et al., *Cell Metabolism.* 2006 July; 4(1):61-73). Each MKP exhibits selectivity towards a particular MAP kinase. For example, while MKP-1 is reported to preferentially dephosphorylate the active forms of p38 and JNK, MKP-3 selectively dephosphorylates ERK. Data from recent studies indicate that mice lacking the MKP-1 gene have increased ERK, p38 and JNK activity (Wu et al., 2006) and cytokine-induced inflammation (Wang and Liu, *Cellular Signaling.* 2007 July; 19(7):1372-82). Thus, MKPs function as negative regulators of pro-inflammatory cytokines.

The following description of the preferred embodiments is merely exemplary in nature and is in no way intended to limit the invention, its application or uses. Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used in this specification and the appended claims, the term "or" is generally employed in its sense including "and/or" unless the content clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, "active" is defined as the agent or agents that provide a therapeutic effect.

As used herein, the term "agent" or "active agent" is meant to encompass any molecule, chemical entity, composition, drug, therapeutic agent, chemotherapeutic agent, or biological agent capable of preventing, ameliorating, or treating a disease or other medical condition. The term includes small molecule compounds, peptides, organic or inorganic molecules, natural or synthetic compounds and the like. An agent can be assayed in accordance with the methods of the invention at any stage during clinical trials, during pre-trial testing, or following FDA-approval. In certain embodiments, the active agent is hemp oil. In other embodiments, the agent is an extract of industrial hemp derived from a cultivar comprising a cannabidiol (CBD) and expressing low levels of tetrahydrocannabinol (THC). In other embodiments, the agent comprises a cannabidiol (CBD), tetrahydrocannabinol (THC) or combinations thereof.

As used herein, the term "cannabinoid" refers to a chemical compound that shows direct or indirect activity at a cannabinoid receptor. There are two main cannabinoid receptors, $CB_1$ and $CB_2$. Other receptors that research suggests have cannabinoid activity include the GPR55 and GPR 18 receptors. The term "phytocannabinoid" refers to cannabinoids that occur in a plant species or are derived from cannabinoids occurring in a plant species. Examples of cannabinoids include, but are not limited to, Tetrahydrocannabinol (THC), Cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), and Cannabigerol Monomethyl Ether (CBGM). It should be understood, that compounds used in the art of pharmaceutics generally serve a variety of functions or purposes. Thus, if a compound named herein is mentioned only once or is used to define more than one term herein, its purpose or function should not be construed as being limited solely to that named purpose(s) or function(s).

As used herein a "derivative" is: a chemical substance that is related structurally to a first chemical substance and theoretically derivable from it; a compound that is formed from a similar first compound or a compound that can be imagined to arise from another first compound, if one atom of the first compound is replaced with another atom or group of atoms; a compound derived or obtained from a parent compound and containing essential elements of the parent compound; or a chemical compound that may be produced from first compound of similar structure in one or more steps.

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

As defined herein, an "effective" amount of a compound or agent (i.e., an effective dosage) means an amount sufficient to produce a (e.g., clinically) desirable result.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. A disease or disorder is "alleviated" if the severity of a symptom of the disease or disorder, the frequency with which such a symptom is experienced by a patient, or both, is reduced.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Oral Compositions Delivering Therapeutically Effective Amounts of Cannabinoids

Many neurological diseases including migraine involve sensitization and activation of neurons (nerve cells) and glial cells. Following activation of neurons there is increased release of mediators that promote inflammation and pain, and thus disrupt normal function. Without wishing to be bound by theory, it was hypothesized that cannabis would inhibit this activation by increasing the proteins in those cells responsible for keeping them quiet and in balance. These proteins are known as phosphatases.

The results from experiments presented in the examples section which follows, which examine the effect of cannabis on cultured trigeminal neurons and glia, evidence that cannabis increases the levels of three major phosphatase proteins in trigeminal neurons and glial cells. The stimulatory effects were both time and dose dependent which means that lower concentrations of cannabis administered for longer times (24 hrs) can produce similar results to higher concentrations for shorter times (2 hrs). This is the first evidence that cannabis can increase the levels of proteins known to protect nerve cells from becoming hyperexcitable. Based on these findings, cannabis would be an effective therapeutic for blocking the inflammation and pain associated with migraine. Furthermore, due to the induction and increase of these specific phosphatase proteins by cannabis, is evidence that cannabis would be an effective therapy for a multitude of inflammatory diseases including epilepsy and even arthritis.

Accordingly, in embodiments the invention provides for compositions comprising therapeutically effective amounts of an active agent comprising: cannabinoids, cannabidiol (CBD), tetrahydrocannabinol (THC), derivatives or combinations thereof.

In certain embodiments, the composition comprises therapeutically effective amounts of one or more therapeutic agents, e.g. Hemp oil, CBD, THC, derivatives thereof or any combinations thereof. In some embodiments, the composition can comprise, in addition to the CBD, THC etc., other types of agents, such as for example, analgesics, antibiotics and the like.

In other embodiments, the compositions are effective in the prevention or treatment of diseases or disorders comprising: inflammatory diseases, neurological diseases, neuroinflammatory diseases, neurodegenerative diseases (e.g. Alzheimer's Disease, Parkinson's Disease, Multiple Sclerosis, etc.), pain, epilepsy, chronic inflammation, inflammation, immunological disorders, autoimmune disorders, atherosclerosis, Chronic obstructive pulmonary disease (COPD), allergy, transplantation, aging, mitochondrial diseases, radiation injury, chemical injury, UV radiation, stress, or combinations thereof. In embodiments, the compositions are effective in reducing, ameliorating or inhibiting pain.

Chewing gum. In certain embodiments, the composition is a chewing gum which releases the active agent(s) during chewing. A suitable chewing gum base comprises one or more constituents including elastomers for elasticity, resins to act as binders and softeners, plasticizers to render the elastomer soft to ensure thorough blending of the gum base and flavors during shelf life. The method for manufacture of a chewing gum is exemplified in US patent application U.S. Ser. No. 14/732,072 filed Jun. 5, 2015, the contents of which are incorporated herein by reference, in its entirety. Briefly, the method comprises initially heating the gum base in ovens to melt the gum base to an internally measured temperature between 140-160° F. The ingredients, including the one or more active ingredients are combined in a mixer. The melted gum base is added to the mixer and cooled to produce a particulate mixture. The temperature of the gum base exceeds that of the mixer when first introduced, but as mixing continues it cools to room temperature and forms granular pieces. These granular pieces are then conditioned for a period of time which allows the granular pieces to dry slightly and complete the crystallization process. The pieces are conditioned for at least about 6 hours at a temperature not greater than about 75° F. and about 60% or less relative humidity. The pieces are then ground into a powder at room temperature with tableting excipients, and tableted. This process preserves the efficacy of the active ingredient or ingredients by avoiding exposure to high heat, mainly during mixing, and extreme cold, mainly during milling, which can otherwise degrade the active ingredient's efficacy.

In some embodiments, a composition based on a chewing gum comprises a therapeutically effective amount of hemp oil, a sugar, a sugar blend, a sugar alcohol, a blend of sugar alcohols, a gum base, or combinations thereof. In certain embodiments, a therapeutically effective amount of hemp oil comprises about 0.1% to about 20% by weight, based on the total weight of the composition. In embodiments, the hemp oil comprises a cannabidiol (CBD) or derivatives thereof of about 0.1% to about 80% by weight.

In other embodiments, the composition comprises: about 10% to about 80% by weight based on the total weight of the composition, of a sugar, sugar blend, sugar alcohol, a blend of sugar alcohols, sugar substitutes, sweetener(s), or combinations thereof, and, about 5% to about 80% by weight based on the total weight of the composition, of a gum base. In certain embodiments, the composition further comprises: flavoring, tableting lubricants and powder flow agents, intensive sweeteners, sugar substitutes or combinations thereof. In certain embodiments, the composition comprises about 1% to about 20% by weight of flavoring, about 0.1% to about 10% by weight of tableting lubricants and powder flow agents, about 0.01% to about 2% by weight of intensive sweeteners and/or sugar substitutes. In embodiments, the sugar or sugar blend comprise dextrose, sucrose, fructose, glucose or combinations thereof. In other embodiments, the sugar alcohol or sugar alcohol blend comprise: sorbitol, isomalt, xylitol, maltitol, mannitol, erythritol or combinations thereof. In other embodiments, a high intensity sweetener comprises sucralose, stevia, honey, monk fruit, neotame, licorice extract or agave nectar. In certain embodiments, the chewing gum composition comprises a flavoring agent, e.g., fruity flavors, menthol flavor, eucalyptus, mint flavor, peppermint flavor, spearmint flavor, and the like. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, banana extract, imitation cherry extract, cherry extract, chocolate extract, pure lemon extract, pure orange extract, pure peppermint extract, imitation pineapple extract, pineapple extract, imitation rum extract, imitation strawberry extract, strawberry extract, pure vanilla extract, or any other flavors; or volatile essential oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee.

In other embodiments, the chewing gum composition comprising the cannabinoid or derivatives thereof further comprises an elastomeric or natural chicle base as is commonly used in chewing gum formulations that are commercially available and accepted by the consumer. The cannabinoid or the derivatives thereof may be comprised by a solid material composed of a cellulose which comprises a well-defined amount of the cannabinoid or the derivative thereof, e.g. in and/or onto voids or pores within the solid material. In certain embodiments, the chewing gum composition has a high initial release rate of the cannabinoid or the derivative thereof to provide a rapid alleviation of pain, nausea, disease symptoms, seizure, inflammation, fever and the like. Accordingly, in certain embodiments, the chewing gum composition releases at least about 1% by weight to about 30% by weight, based on the total weight content of the cannabinoid or the derivative thereof in the chewing gum composition, within about thirty seconds to about five minutes after ingestion.

An elastomeric or natural chicle base is normally present in the chewing gum composition in an amount of about 10% to about 85% by weight, based on the total weight of the chewing gum composition.

Lozenges. In another embodiment, the composition is a lozenge which releases the active agent(s) over a period of time, e.g. from about 1 minute or more, once it is in the subject's mouth. In another embodiment, the composition is a fast dissolving lozenge which dissolves in less than about 1 minute in the oral cavity or sublingually. The lozenges are formulated to administer a dose of about 1 to 500 mg of the active agent per application directly to the blood stream via adsorption through the buccal or oral mucosa.

Accordingly, in certain embodiments, a composition for a lozenge comprises a sugar, a sugar blend, sugar alcohol, a blend of sugar alcohols, sweeteners, a bulk filler, a cannabinoid and/or derivatives thereof, flavorings, tableting lubricants, powder flow agents or combinations thereof. In certain embodiments, the composition comprises, based on the total weight of the composition: about 10% to about 80% by weight of a sugar, a sugar blend, sugar alcohol, blend of sugar alcohols, sweetener, or combinations thereof, about 5% to about 50% by weight of bulk filler, about 0.1% to about 20% by weight of a cannabinoid or derivatives thereof, about 0.1% to about 10% by weight of a flavor powder or flavoring, about 0.1% to about 10% by weight of tableting lubricants and powder flow agents, or combinations thereof.

In one embodiment, the composition, based on the total weight of the composition, comprises: about 55% to about 70% by weight of a sugar, a sugar blend, sugar alcohol, blend of sugar alcohols, sweetener, or combinations thereof, about 5% to about 40% by weight of bulk filler, about 0.1% to about 10% by weight of a cannabinoid or derivatives thereof, about 0.1% to about 5% by weight of a flavor powder or flavoring, about 0.1% to about 5% by weight of tableting lubricants and powder flow agents, or combinations thereof. In certain embodiments, the sugar or sugar blend comprise dextrose, sucrose, fructose, glucose or combinations thereof. In other embodiments, the sugar alcohol or sugar alcohol blend comprise: sorbitol, isomalt, xylitol, maltitol, mannitol, erythritol or combinations thereof and the high intensity sweetener comprises sucralose, aspartame, acesulfame potassium, stevia, honey or agave nectar.

In one embodiment, the tableting lubricants and powder flow agents comprises magnesium stearate, silicon dioxide, calcium stearate, stearic acid, talc, rice bran-based excipients like Nu-Rice and Nu-Flow, or combinations thereof.

In other embodiments, a bulk filler comprises microcrystalline cellulose (MCC), bamboo fibers, or combinations thereof. In order to manufacture a slower versus fast-dissolving lozenge or tablet, the proportion of the bulk fillers are increased or decreased relative to the other constituents to alter the dissolution rate of the lozenge, i.e. fast-dissolving, slow dissolving etc. The bulk fillers absorb moisture quickly which creates the dissolution. Suitable fillers include celluloses and cellulose derivatives including microcrystalline cellulose, hydroxypropylcellulose and sodium carboxymethylcellulose, lactose, starches including potato starch and corn starch, carbohydrates including a cellulose derivative, e.g. hemicellulose. The cellulose derivative may be of natural origin, e.g. dextran, agarose, agar, pectin, alginate, xanthan, chitosan, starch. The cellulose derivative may also be of synthetic or semi-synthetic origin. In certain embodiments, a bulk filler comprises microcrystalline cellulose (MCC), bamboo fibers, or combinations thereof. The bulk fillers are present in the composition from about 5% to about 50% by weight of bulk filler, based on total weight of the composition. Specific examples of a suitable microcrystalline cellulose is microcrystalline cellulose comprising: AVICEL™ grades PH-100, PH-102, PH-103, PH-105, PH-112, PH-113, PH-200, PH-300, PH-302, VIVACEL™ grades 101, 102, 12, 20 and EMOCEL™ grades 50M and 90M, and the like, and mixtures thereof.

Flavors, coloring agents, spices, and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee.

Other formulations. The active agents may further be formulated with acceptable excipients and/or carriers for oral consumption. The carrier may be a liquid, gel, gelcap, capsule, powder, solid tablet (coated or non-coated), tea, or the like. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers further include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Mack Publishing Co., Easton, Pa.). Such formulations may preferably comprise from about 1 mg to 500 mg of the concentrate. Where the formulation is an oral delivery vehicle such as a capsule or tablet, the oral delivery vehicle may comprise from about 0.1 to 500 mg of the concentrate, 10 to 200 mg of the concentrate to 10 to 100 mg of the concentrate. A daily dosage may comprise 1, 2, 3, 4 or 5 of the oral delivery vehicles.

In other embodiments, the active agents are provided as a powder or liquid suitable for adding by the consumer to a food or beverage. For example, in some embodiments, the concentrate can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

In other embodiments, the compositions comprising the cannabinoids or derivatives thereof, further comprise one or more additional bioactive agents, phytonutrients, or nutraceutical agents to provide a dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms. Nutraceutical agents are natural, bioactive chemical compounds that have health promoting, disease preventing or medicinal properties. Examples of nutraceutical agents that may be combined with the concentrates of the present invention include, but are not limited to, resveratrol, fucoidan, Allium cepa, Allium sativum, Aloe vera, Angelica Species, Naturally Occurring Antioxidants, Aspergillus oryzae, barley grass, Bromelain, Carnitine, carotenoids and flavonoids, Catechin, Centella asiatica (Gotu kola), Coenzyme Q10, Chinese Prepared Medicines, Coleus forskohlii, Commiphora mukul, Conjugated Linoleic Acids (CLAs), Crataegus oxyacantha (Hawthorne), Curcuma longa (Turmeric), Echinacea Species (Purple Coneflower), Eleutherococcus senticosus (Siberian Ginseng), Ephedra Species, Dietary Fish Oil, Genistein, Ginkgo biloba, Glycyrrhiza (Licorice), Hypericum perforatum (St. John's Wort), Hydrastis (Goldenseal) and other Berberine-containing plants, Lactobacillus, Lobelia (Indian Tobacco), Melaleuca alternifolia, Menaquinone, Mentha piperita, n-glycolylneuraminic acid (NGNA), Panax Ginseng, Pancreatic Enzymes, Piper mythisticum, Procyanidolic Oligomers, Pygeum africanum, Quercetin, Sarsaparilla species, Serenoa repens (Saw palmetto, Sabal serrulata), Silybum marianum (Milk Thistle), Rosemary/Lemon balm, Selenite, Tabebuia avellanedae (La-Pacho), Taraxacum officinale, Tanacetum parthenium (Feverfew), Taxol, Uva ursi (Bearberry), Vaccinium myrtillus (Blueberry), Valerian officinalis, Viscum album (Mistletoe), Vitamin A, Beta-Carotene and other carotenoids, and Zingiber officinale (Ginger).

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

Manufacture

The various compositions embodied herein can be manufactured using known methods.

In some embodiments, the compositions embodied herein are manufactured using 3-Dimensional (3-D) printing methods. Suitable equipment assemblies for three-dimensional printing of articles are commercially available or are already in use: Massachusetts Institute of Technology Three-Dimensional Printing Laboratory (Cambridge, Mass.), Z Corporation's 3DP and HD3DP.™. systems (Burlington, Mass.), The Ex One Company, L.L.C. (Irwin, Pa.), Soligen (Northridge, Calif.), Specific Surface Corporation (Franklin, Mass.), TDK Corporation (Chiba-ken, Japan), Therics L.L.C. (Akron, Ohio, now a part of Integra Lifesciences), Phoenix Analysis & Design Technologies (Tempe, Ariz.), Stratasys, Inc.'s Dimension™ system (Eden Prairie, Minn.), Objet Geometries (Billerica, Mass. or Rehovot, Israel), Xpress3D (Minneapolis, Minn.), and 3D Systems' INVISION™ system (Valencia, Calif.). Other suitable 3DP systems are disclosed in U.S. No. 20080281019, Nos. 20080277823, 20080275181, 20080269940, 20080269939, 20080259434, 20080241404, 20080231645, 20080229961, 20080211132, 20080192074, 20080180509, 20080138515, 20080124464, 20080121172, 20080121130, 20080118655, 20080110395, 20080105144, 20080068416, 20080062214, 20080042321, 20070289705, 20070259010, 20070252871, 20070195150, 20070188549, 20070187508, 20070182799, 20070182782, 20060268057, 20060268044, 20060230970, 20060141145, 20060127153, 20060111807, 20060110443, 20060099287, 20060077241, 20060035034, 20060030964, 20050247216, 20050204939, 20050179721, 20050104241, 20050069784, 20050061241, 20050059757, 20040265413, 20040262797, 20040252174, 20040243133, 20040225398, 20040183796, 20040145781, 20040145628, 20040143359, 20040141043, 20040141030, 20040141025, 20040141024, 20040118309, 20040112523, 20040012112, 20040005360, 20040005182, 20040004653, 20040004303, 20040003741, 20040003738, 20030198677, 20030143268, 20020125592, 20020114652, 20020079601, 20020064745, 20020033548, 20020015728, 20010028471, and No. 20010017085; U.S. Pat. Nos. 5,490,962, 5,204,055, 5,121,329, 5,127,037, 5,252,264, 5,340,656, 5,387,380, 5,490,882, 5,518,680, 5,717,599, 5,851,465, 5,869,170, 5,879,489, 5,934,343, 5,940,674, 6,007,318, 6,146,567, 6,165,406, 6,193,923, 6,200,508, 6,213,168, 6,336,480, 6,363,606, 6,375,874, 6,508,971, 6,530,958, 6,547,994, 6,596,224, 6,772,026, 6,850,334, 6,905,645, 6,945,638, 6,989,115, 7,220,380, 7,291,002 7,365,129, 7,435,368, 7,455,804, 7,828,022, 8,017,055; PCT International Publications No. WO 00/26026, No. WO 98/043762, No. WO 95/034468, No. WO 95/011007; and European Patent No. 1,631,440, which employs a cylindrical (radial or polar) coordinate-based system due to its construction. The entire disclosure of each of these references is hereby incorporated herein.

A 3-D printing process has been described in U.S. Pat. Nos. 9,339,489; 9,314,429; 8,888,480; 8,828,411, the contents of which are incorporated herein. In some of these processes, a powder layering system is used that forms a layer of powder and printing system that applies a printing fluid to the layer of powder according to a predetermined pattern, thereby forming an incremental printed layer. The printing fluid serves to form bound particles of powder, i.e. particles that are adhered to one another by one or more pharmaceutical excipients and/or one or more active ingredients. Incremental printed layers are formed one on top of another to vertically build the dosage form of the invention, thereby forming a dosage form comprising plural incremental printed layers. The process of spreading powder and depositing droplets is repeated until the desired number of layers for the dosage form is complete. The layers adhere to one another due to bleeding of printing fluid from one layer to an adjacent other layer such that one or more excipients and/or one or more active ingredients adhere to both adjacent layers. Following completion of the initial three-dimensional structure, residual printing fluid is removed from or reduced in the dosage form by drying. The evaporation of solvent during the drying process leaves a matrix having a three-dimensional architecture comprising the particles of bulk material bound by solidified binder and/or other components including one or more active ingredients and/or any optional pharmaceutically acceptable excipients.

The three-dimensional printing process is normally conducted at ambient temperatures. The process can utilize a variety of printing fluids, including biologically compatible organic and aqueous solvents. The process is additive, whereby microscopic features are incorporated layer by layer, allowing a wide range of possible architectures to be constructed precisely on a sub-millimeter scale. Using three-dimensional printing to control simultaneously both the microscopic features and the macroscopic shape, the unique drug delivery systems of the present invention are obtained.

A particularly suitable printing assembly for three-dimensional printing of the instant dosage form is described in U.S. application No. 61/696,839, filed Sep. 5, 2012, the disclosure of which is hereby incorporated by reference in its entirety. The assembly includes build modules each having an incrementally height adjustable platform disposed within a cavity of the build modules, a powder layering system, a printing system, a printing fluid removal system and a dosage form handling system.

In general, at least two components are used in the three-dimensional printing process used to prepare the matrix of the rapidly dispersing dosage forms. The first component is the bulk powder material to be included in the incremental powder layers. The second component is the printing fluid (in some cases the fluid may also contain a binder) that is dispensed by a printhead onto the powder layer. In some embodiments, the bulk powder material is comprised of one or more pharmaceutically acceptable excipients, cannabinoids or derivatives thereof, disintegrant, binder and surfactant.

At least one component of the matrix must serve as a "binding agent" that binds particles of bulk powder together in the completed three-dimensional matrix. The binding agent produces adhesion between particles of the bulk powder. It is this adhesion that enables the dosage form to maintain a fixed shaped (geometry) and maintain its characteristics of hardness and friability adequate to permit handling and storage. The strength and extent of the particle binding depends on the proportion of the binding agent either in the powder layer or dissolved in the solvent, and is a function of the amount of fluid deposited. The term adhesion means the bonding or binding of particles of the bulk material to each other or to particles of another material present, such as particles of binder or active ingredient. There are various ways in which a binding agent can be included in the matrix.

The physical properties of the dosage form can be controlled by varying incremental powder layer thickness, powder composition, printing fluid composition, printing fluid saturation level (print density) on a layer, and identity and amount of the excipients included within the dosage form, e.g. identity and amount of disintegrant, binder, sweetener, surfactant. These variables exhibit different levels of effect upon dosage form hardness, bulk density, disintegration time, dissolution time, bioavailability, moisture content, mouthfeel and friability.

Three-dimensional printing can have spatial descriptors in each of three different, typically orthogonal directions. In three-dimensional printing, fluid may be deposited in drops or in fluid units resembling drops. Drops may be deposited in a succession that forms a line corresponding to the motion of the printhead. The spacing between those drops is the drop-to-drop spacing. After completion of one line, another line may be deposited adjacent to the earlier-deposited line and separated from the earlier-deposited line by a distance that is a line-to-line spacing. After completion of printing on a layer of powder, another powder layer may be deposited, with each powder layer having a layer thickness. The powder layer thickness is the third descriptor.

In some instances, the spacing of droplets may be described in terms of the resolution of the printing system, often expressed as dots per inch (dpi), which is the reciprocal of droplet spacing. For example, resolutions of 300 and 600 dpi correspond to droplet spacing's of about 84.7 microns and about 42.3 microns, respectively. The drop-to-drop spacing (within a line), or the line spacing (spacing of droplets from one line to the next), or any other spacing of droplets may be described in terms of resolution expressed in dpi. In some instances, layer-by-layer instructions for making the dosage forms may consist of a series of pixelated images characterized by a resolution in dots-per-inch in each of two orthogonal linear directions. In some instances, these pixelated images are 1-bit monochrome images, alternately referred to as binary or bi-level images in which each pixel contains one bit of information (0 or 1) that may be represented as either black or white onscreen.

In some instances, the relative amount of binding in localized regions of the dosage form is achieved by "grayscaling" (i.e., use of a grayscale print pattern) in the dosage form design. In the case of 1-bit monochrome images used for machine instructions, grayscaling is achieved by changing the number of "black" pixels relative to "white" pixels in a chosen region of a dosage form, or in a chosen layer of a dosage form, or throughout a dosage form. Any other regions that may be "solid" by using all black pixels. In some embodiments, the dosage form design includes a "solid" exterior and a "grayscaled" interior. In some embodiments, grayscaling may be achieved with equally spaced black pixels amongst white pixels to reach an overall ratio of black to white pixels in the grayscaled region. In other embodiments, grayscaling may be achieved with randomly placed black pixels amongst white pixels to achieve an overall ratio of black to white pixels in the grayscaled region. In still other embodiments, grayscaling may be achieved with a chosen pattern (e.g., parallel lines, hashed pattern, dot pattern) of black pixels amongst white pixels to achieve an overall ratio of black to white pixels in the grayscaled region.

In three-dimensional printing, a voxel or unit volume may be defined by one drop-to-drop spacing in the fast axis direction of motion, by one line-to-line spacing in the slow axis direction of motion, and by one layer thickness in the vertical direction. Some of this unit volume is occupied by powder particles, and the remainder of the unit volume is empty space that collectively has a volume that is the void volume.

The saturation level (print density) describes how much of the void space in this unit volume is occupied by liquid which is dispensed in a drop or fluid unit which is dedicated to that particular voxel. The saturation level is the ratio of the dispensed fluid volume to the volume of empty space in the voxel. In general, in three-dimensional printing, saturation levels may be chosen to be slightly less than, or somewhere approximately equal to, 1.0, also expressed as 100%. Excessively low saturation levels tend to result in poor structural integrity. Excessively high saturations levels tend to result in excessive bleeding of liquid beyond where the liquid was deposited.

Suitable printing devices include those having a continuous jet printhead or those having a drop-on-demand printhead. A continuous jet printhead provides a continuous jet (spray) of droplets while depositing printing fluid onto a powder layer. A drop-on-demand printhead only deposits droplets of printing fluid onto the powder layer if it receives an instruction (demand, operational command) to do so. A printhead scans (applies fluid to) the surface of powder layer from left to right at a predetermined rate, e.g. a scan rate, to form a line of droplets. A high scan rate will result in a lower saturation level, and a low scan rate with result in a higher saturation level when comparing printing fluid deposition at a constant volume per unit time. When considering the situation where binder is present in the binding solution, an increase in the print speed from 1.0 m/s to 2.0 m/s reduces the total volume of binder solution deposited in the tablets by half. As the print speed increases, the bulk density (theoretical, calculated from the weight and dimensions of the tablet) decreases. A simultaneous decrease in the dimensions and weight of the tablets is also seen. This decrease is attributed to the fact that a decrease in the total volume of binder droplets deposited onto the powder results in a decrease in the extent of binder solution spreading in the powder. Increasing the print speed also decreases the flash time and the hardness and increases the friability of the tablets. This result is obtained because the proportion of binder decreases in the tablets as the print speed increases. An increase in the print speed also increases the void volume inside the tablets.

When using a continuous jet printhead, the printhead scans at a rate of about 0.5 to 3.0 m/sec. When using a drop-on-demand jet printhead, the printhead scans at a rate of 0.1 to 1 m/sec.

The volume of individual droplets can be varied as desired, for example, by selection of a different three-dimensional printing machine, or different printhead components on the same machine, or different parameters on the same printhead and same machine. Increasing the volume of the droplet increases the saturation level and decreasing the volume of a droplet decreases the saturation level when comparing printing fluid deposition at a constant scan rate. When using a continuous jet printhead, the size of the fluid droplets delivered by the printhead ranges from about 15 μm to about 150 μm in diameter. When using a drop-on-demand printhead, the size of the fluid droplets delivered by the printhead ranges from about 50 μm to about 500 μm in diameter.

The flow rate of the fluid delivered by the printhead can be varied as desired. Increasing the flow rate increases the saturation level and decreasing the flow rate decreases the saturation level when comparing printing fluid deposition at a constant scan rate.

The powder layering system and the height adjustable platform cooperate to form thin incremental layers of powder in the build modules. The total thickness (height) of the dosage form will be a function of the number and thickness of the incremental layers. The number of printed incremental layers typically ranges from 5 to 50. A matrix will typically comprise (consist essentially of or consist of) 20 to 50, 20 to 40, 25 to 40, 30 to 40 or 30 to 35 printed incremental layers. The "end" section of a dosage form will typically comprise 1 to 10, 1 to 7, 2 to 7, 2 to 5, or 4 to 6 printed incremental layers. An end section with an indicium will typically comprise 2 to 10, 2 to 7, 2 to 5, or 4 to 7 printed incremental layers. The balance of the printed incremental layers will comprise the middle portion, with respect to the vertical height, of the dosage form. The middle portion will typically comprise 5 to 40, 10 to 30, 10 to 20, or 20 to 30 printed incremental layers. The incremental layers are of a predetermined height (vertical thickness), which typically varies from 0.005 to 0.015 inches, 0.008 to 0.012 inches, 0.009 to 0.011 inches, about 0.01 inches, 100-300 μm, 100-500 μm, about 200 μm, or about 250 μm. As thicker incremental layers are used, an increasing amount of printing fluid must be deposited on that layer to ensure adequate binding both within the plane of the layer and layer-to-layer. Conversely, for a thinner incremental layer a lesser amount of printing fluid must be deposited to obtain the same extent of binding. For a given amount of printing fluid deposited per layer, using a larger layer thickness will reduce (worsen) dosage form handleability and reduce (improve) dispersion time. If too thick of a layer is used for a given amount of fluid, laminar defects may form that cause the dosage form to easily fracture along the plane of the layers (delamination), or the dosage form itself may not have adequate strength to handle at all. In some embodiments, the thickness of the incremental layers ranges from 100-400 microns, 150-300 microns, or 200-250 microns. In one preferred embodiment, the layer thickness is 200 microns. In another preferred embodiment, the layer thickness is 250 microns.

One or more pharmaceutically acceptable excipients can be included in bulk powder material and/or the printing fluid. Each excipient may be independently selected upon each occurrence from a water soluble, aqueous fluid soluble, partially water soluble, partially aqueous fluid soluble, water insoluble or aqueous fluid insoluble excipient as needed to provide the required particle-to-particle binding in a printed matrix.

Most pharmaceutically acceptable excipients, both small molecules and polymers, can be employed, which allow a pharmaceutically active ingredient to be loosely encased in a porous structure (a matrix of bound particles) that is subject to rapid dispersion in the presence of an appropriate aqueous fluid, e.g., saliva. Some of these excipients, suitable for use in the three-dimensional printing process of the invention, are listed in the Handbook of Pharmaceutical Excipients (Eds. A. Wade and P. J. Weller, Second edition, American Pharmaceutical Association, The Pharmaceutical Press, London, 1994).

Suitable types of excipients include binder, disintegrant, dispersant, sweetener, glidant, flavorant, surfactant, humectant, preservative, antioxidant and diluent. Although conventional pharmaceutical excipients may be used, they may not always function in precisely the same manner as with traditional pharmaceutical processing.

One or more binders can be included in the printed matrix. The binder may be included in either the powder material or in the printing fluid dispensed through the printhead. The binder is independently selected upon each occurrence. Adhesion of the particles to and/or by the binder occurs either when the binder is contacted by the printing fluid from the printhead or when it is present (i.e., soluble) in the printing fluid. The binder is preferably water soluble, aqueous fluid soluble, partially water soluble or partially aqueous fluid soluble.

Suitable binders include water-soluble synthetic polymer, polyvinlypyrrolidone (povidone), sorbitol, mannitiol, xylitol, lactitol, erythritol, pregelatinized starch, modified starch, hydroxypropylmethylcellulose and others. The preferred binder is polyvinylpyrrolidone, e.g. PVP K30, modified starch (e.g., starch sodium octenylsuccinate), mannitol or a combination thereof. PVP with a K value different from 30 may be used, including without limitation PVP K25 and PVP K90.

The following materials are considered binders, even though they exhibit low strength binding: spray dried lactose, fructose, sucrose, dextrose, sorbitol, mannitol, or xylitol.

One or more disintegrants can be included in the printed matrix. The disintegrant can be present in the bulk powder. The disintegrant is independently selected upon each occurrence. In some embodiments, the bulk powder comprises 5 to 30% wt, 10 to 25% wt, 15 to 25% wt, 18 to 24% wt, 18 to 23.7% wt, 1-30% wt, 10-25% wt, 20-25% wt of disintegrant. Suitable disintegrants include microcrystalline cellulose (MCC), crospovidone (cross-linked polyvinylpyrrolidone), croscarmellose, sodium starch glycolate or a combination thereof. The preferred disintegrant is microcrystalline cellulose. The binder and disintegrant are key ingredients for controlling the hardness, friability and dispersion time of the matrix. The greater the amount of binder, the higher the hardness, the lower the friability and the slower the dispersion time. On the other hand, increasing the amount of disintegrant provides lower hardness, increased friability and a faster dispersion time. Accordingly, the matrix of the invention comprises a balanced amount of binder and disintegrant.

One or more sweeteners can be included in the printed matrix. The sweetener can be present in the bulk powder and/or in the printing fluid applied to the bulk powder. Better taste-masking is observed when at least one sweetener is present in at least the printing fluid. The sweetener is independently selected upon each occurrence. The printing fluid and the bulk powder can have at least one sweetener in common, e.g. the printing fluid and bulk powder each comprise the same sweetener and the bulk powder comprises an additional sweetener. The sweetener is present in at least the printing fluid and can also be present in the bulk powder.

One or more flavorants can be included in the matrix. The flavorant can be present in the bulk powder and/or the printing fluid. The flavorant is independently selected upon each occurrence. The flavorant is preferably water soluble, aqueous fluid soluble, partially water soluble or partially aqueous fluid soluble. In some embodiments, the flavorant may be provided on a powdered carrier. Suitable carriers may be chosen from starches, celluloses, and other excipients on which the flavorant could be absorbed, adsorbed, encapsulated, or otherwise loaded.

One or more surfactants can be included in the printing fluid and/or bulk powder. The surfactant is independently selected upon each occurrence. Suitable surfactants include polysorbate (PEG-ylated sorbitan (a derivative of sorbitol) esterified with fatty acid), poloxamer or a combination thereof. Suitable polysorbates include polysorbate 20 (Polyoxyethylene (20) sorbitan monolaurate), polysorbate 40 (Polyoxyethylene (20) sorbitan monopalmitate), polysorbate 60 (Polyoxyethylene (20) sorbitan monostearate), polysorbate 80 (Polyoxyethylene (20) sorbitan monooleate), sodium lauryl sulfate, poloxamer (comprising a central (poly(propylene oxide)) flanked by two chains of (poly(ethylene oxide), e.g. LUTTROL), low molecular weight polyethylene glycol (e.g. PEG 400). Suitable poloxamers may include poloxamers 124, 188, 237, 338, or 407.

Even though the dosage form can be preservative-free, one or more preservatives may optionally be included in the printing fluid or powder blend. Suitable preservatives include antifungal or antimicrobial preservatives such as methylparaben and proprylparaben. In some embodiments, the printing fluid comprises 0.001 to 0.2% preservative.

One or more glidants can be included in the bulk powder. In some embodiments, the bulk powder comprises 0.1-2.0%, 0.25-1.5%, or 0.5-1.0% wt of glidant. Suitable glidants include fumed silica (colloidal silicon dioxide).

The matrix may also comprise glycerin (glycerol) introduced therein either by way of the bulk powder or the printing fluid. Glycerin can exhibit characteristics of a humectant, sweetener, preservative, lubricant, saponifier or solvent. The present inventors have discovered that glycerin unexpectedly behaves contrary to other excipients when included in a three-dimensionally printed dosage form. As noted above, increasing the amount of other excipients disclosed generally results in increased hardness with concomitantly increased disintegration time; however, increasing the amount of glycerin results in increased hardness but unexpectedly reduced disintegration time. The ability of glycerin to behave in this manner is particularly advantageous and has not been observed with any other material incorporated into a three-dimensionally printed orodispersible dosage form.

In some embodiments, glycerin is included in the printing fluid. The printing fluid can comprise 55-95% wt, 60-85% wt or 65-75% wt of water or aqueous buffer. The printing fluid can comprise 1-25% wt, 5-20% wt or 10-15% wt of at least one organic solvent. A suitable organic solvent is alcohol. Suitable alcohols include ethanol, methanol, propanol, isopropanol, or a combination thereof. In some embodiments, the alcohol is ethanol. In some embodiments, the solvent is isopropanol.

Effective Doses

Effective doses of the compositions of the present invention, for the treatment of the above described diseases, vary depending upon may different factors, including means of administration, physiological state of the patient, whether the patient is human or an animal, other medications administered, and whether treatment is prophylactic or therapeutic. Usually, the patient is a human.

The compositions can be administered on multiple occasions, wherein intervals between single dosages can be hourly, daily, weekly, monthly, or yearly. Alternatively, one or more of the compounds of the invention can be administered as a sustained-release formulation, in which case less frequent administration is required. Dosage and frequency may vary depending on the half-life of the compounds of the invention. In therapeutic applications, a relatively high dosage at relatively short intervals is sometimes required until progression of the disease is reduced or terminated, and sometimes until the patient shows partial or complete amelioration of symptoms of the disease. Thereafter, the patient can be administered a prophylactic regime.

For any active agent used in the methods of the invention, the therapeutically effective amount or dose can be estimated initially from activity assays in cell cultures and/or animals. For example, a dose can be formulated in animal models to achieve a circulating concentration range that includes the $IC_{50}$ as determined by activity assays (e.g., the concentration of the test compound, which achieves a half-maximal inhibition of the proliferation activity). Such information can be used to more accurately determine useful doses in humans.

The dosage may vary depending upon the dosage form employed. Dosage amount and interval may be adjusted individually to provide plasma levels of the active moiety which are sufficient to maintain therapeutic effects, termed the minimal effective concentration (MEC). The MEC will vary for each preparation, but can be estimated from in vitro and/or in vivo data (see, for example, the examples section which follows). HPLC assays or bioassays can be used to determine plasma concentrations. Dosage intervals can also be determined using the MEC value. Preparations should be administered using a regimen, which maintains plasma levels above the MEC for 10-90% of the time, preferable between 30-90% and most preferably 50-90%. Depending on the severity and responsiveness of the condition to be treated, dosing can also be a single administration of a slow release composition described hereinabove, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, etc.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All publications and patent documents cited in this application are incorporated by reference for all purposes to the same extent as if each individual publication or patent document were so individually denoted. By their citation of various references in this document, applicants do not admit any particular reference is "prior art" to their invention.

EXAMPLES

The following non-limiting Examples serve to illustrate selected embodiments of the invention and which do not limit the scope of the invention described in the claims. It will be appreciated that variations in proportions and alternatives in elements of the components shown will be apparent to those skilled in the art and are within the scope of embodiments of the present invention.

Example 1

Administration of a Cannabinoid Enriched Extract Expressing Low Levels of THC Stimulates Increased Expression of MAP Kinase Phosphatases in Trigeminal Ganglion Neurons and Glia: Implications for Migraine Therapy The effects of a cannabidiol (CBD) extract of industrial hemp derived from a cultivar expressing low levels of Tetrahydrocannabinol (THC) on the levels of MAP kinase phosphatases in trigeminal ganglion, upper spinal cord, and brain as well as changes in cognitive ability, were investigated.

Objectives: (i) Determine the effect of cannabis on MAP kinase phosphatases (MKPs) in the trigeminal and dorsal root ganglia. (ii) Investigate the effect of cannabis on MKPs in the lower and upper spinal cord. (iii) Study the effect of cannabis on MKPs in the brain (with focus on regions affected by epilepsy and traumatic brain injury). (iv) Demonstrate that cannabis with minimal Tetrahydrocannabinol (THC) does not impair cognitive abilities.

Clinical Relevance: Data from these studies identify sites within the peripheral and central nervous system that are responsive to cannabis and cause increased expression of MKPs. Results from this study provide evidence into therapeutic uses for cannabis in treating neurological diseases that involve inflammatory reactions mediated by neurons and/or glial cells.

Methods

Animals. The animal care and procedures are conducted in accordance with institutional and National Institutes of Health guidelines. Adult male or female Sprague-Dawley rats (Charles River Laboratories Inc., Wilmington, Mass.) are housed in clean plastic cages on a 12-hour light/dark cycle with unrestricted access to food and water.

Cannabis treatment. Adult male or female Sprague-Dawley rats were injected with 2 different doses of a CBD (1 mg/kg and 0.1 mg/kg). After 2, 24, and 48 hours, animals were sacrificed and the trigeminal ganglia, upper spinal cord (C1-3), and the whole brain were removed for further analysis. The experimental design included a minimum of five animals for each condition—naïve unstimulated, vehicle control, and two concentrations of CBD. Immunohistochemistry and image analysis was used to determine the levels of the MAP kinase phosphatases MKP-1, MKP-2, and MKP-3 in ganglia, spinal cord, and brain tissues. In addition, two different cognitive tests were performed including novel object recognition and spatial reference memory, which is known as the Morris Water Maze test.

Immunohistochemical analysis. Immunohistochemistry and image analysis was conducted essentially as described in previous studies (Cady and Durham, *Brain Res.* 2010 Apr. 6; 1323:18-32; Cady et al., Headache. 2011 July-August; 51(7):1078-86). Briefly, ganglia, spinal cord, and brain tissues were placed in a solution of 4% paraformaldehyde overnight at 4° C. Following paraformaldehyde fixation, tissues were incubated in 15% sucrose in distilled water at 4° C. for 1 hour and then 30% sucrose overnight at 4° C. Ganglia were mounted in OCT (Sakura Finetek, Torrance, Calif.) such that the ventral surface was in contact with a Superfrost Plus slide (Fisher Scientific, Pittsburgh, Pa.), quickly frozen, and stored at −20° C. Fourteen micron longitudinal sections of the entire trigeminal ganglion tissue were serially prepared using a cryostat (Microm HM 525, Thermo Scientific, Waltham, Mass.) set at −24° C. Sections from the middle of the ganglion, which contained cell bodies from all three branches, were chosen for immunohistochemistry. For the spinal cord samples, tissues were positioned with the caudal side in contact with the slide, covered with OCT, and quickly frozen. Spinal cord sections (14 μm) containing the spinal trigeminal nucleus (STN) were sectioned transversely at a distance of 4-5 mm posterior to the obex or from the L4/L5 region of the spinal cord using a cryostat set at −24° C. The brain tissue was hemi-sected and then sectioned in a dorsal/ventral plane to allow easy identification of the cortex and hippocampus.

Slides containing sections of ganglia, spinal cord, or brain were incubated in a solution of 0.1% Triton X-100 and 5% donkey serum (Jackson Immuno Research Laboratories, West Grove, Pa.) for 30 minutes. Next, sections were incubated with primary antibodies (see below) either for 3 hours at room temperature or overnight at 4° C. and then with secondary antibodies for 1 hour at room temperature. As a control, some sections were incubated with only secondary antibodies. Sections were mounted using Vectashield medium (H-1200) containing 4', 6-diamidino-2-phenylindole (DAPI; Vector Laboratories, Burlingame, Calif.) to co-stain cell nuclei. Images (200×) were collected using a Zeiss Axiocam mRm camera mounted on a Zeiss Imager Z2 fluorescent microscope equipped with an Apo-Tome. Image acquisition was performed using Zeiss Zen Blue 2011 (Thornwood, N.Y.).

Antibodies. (i) Primary antibodies directed against proteins implicated in development of peripheral and central sensitization: MKP-1, MKP-2, and MKP-3. (ii) Primary antibodies directed against proteins used as markers of neurons (NeuN and/or NF-160) and glia (GFAP and Iba 1 or OX42). (iii) Secondary antibodies conjugated to fluorescent dyes.

Quantification of staining intensity. The relative staining intensity measurements in trigeminal ganglia and spinal cord tissues was based on this laboratory's previously published protocols (Cady and Durham, 2010, Cady et al., 2011). For trigeminal ganglia, four randomly chosen 200× images containing a similar number of cells as identified by DAPI, were analyzed for each experimental condition, which was repeated in at least 3 independent experiments, resulting in a minimum of 12 fluorescent images being analyzed for the intensity measurements. Two researchers blinded to the experimental conditions independently performed the measurements. The fluorescent staining intensity in spinal cord tissue was determined by measuring the mean gray intensity from four regions, in laminas I-III, of staining in the medullary horn and subtracting the intensity from acellular regions of the medullary horn. The fold-change in staining intensity was defined as the mean change in relative intensity in the experimental condition when compared to the mean of the unstimulated control tissue that was made equal to one. Changes in immunostaining intensity were evaluated using the Mann-Whitney U test. For all studies, results were considered significant when $P<0.05$. All statistical tests were performed using SPSS (Version 20, IBM, Chicago, Ill.). Results are reported as mean±SEM.

Behavioral Studies—Cognitive.

These studies were conducted to clearly demonstrate that cannabis with low amounts of THC do not impair cognitive function in traditional cognition experimental models. A minimum of 8 animals per condition was used in these studies.

Novel Object Recognition. This test utilizes rodent's spontaneous preference for novelty to measure short term memory. In this assay animals are allowed to become familiar with two identical objects. At this time, one object is removed from the testing area and replaced with a novel object. The time the animal explores the novel object verses the familiar one is measured, and reported as a percentage. An increased time in exploration of the novel object is attributed to the animals' memory that he has already explored the other object. The opposite outcome would be interpreted as the animal has forgotten or failed to create a memory that it has already explored the familiar object. This assay is designed to assess the ability to create memories and is similar to episodic memory in humans that relies on the peri- and post-rhinal regions rather than the hippocampus.

Spatial Reference Memory: The Morris Water Maze. This assay relies on the rodents' natural ability to find and remember locations using external clues, or the development of a spatial map of their environment. This assay is the most widely used and accepted methods to study this type of learning. The basic setup consists of a circular tank filled with water rendered opaque by diluted inert paint. Animals are placed in the water and swim until they stumble upon and climb on a slightly submerged, and therefore invisible platform. On subsequent trials, animals learn to find the platform, always placed in the same position, more and more efficiently, aided by the visual cues available in the room. Training sessions consist of at least 4 trials (with each trial starting at a different location along the perimeter of the pool) and are typically repeated over a period of a few days. Performance can be assessed during training by measuring the distance covered and the time elapsed searching the escape platform. Importantly, in a final probe trial, the platform is removed from its usual location, and the time spent by the animal searching for the platform at the expected location is interpreted as a measure of spatial, hippocampus-dependent memory.

Statistical analysis was performed using a non-parametric Mann-Whitney U test and SPSS 20 software. Differences were considered to be significant at $P<0.05$.

Results

Data from Cell Culture Studies: Cannabis treatment of cultures of trigeminal ganglia containing both neurons and glial cells was able to dose and time-dependently increase the expression of MKP1, MKP2, and MKP3. Treatment with cannabis increased expression of MKP1 when compared to levels in unstimulated control cultures. The CBD had the greatest effect on MKP-2 and MKP-3 levels in the upper spinal cord tissue which contained the site where primary neurons that provide sensory innervation of the head and face synapse with second order nociceptive neurons. In the trigeminal ganglion, the CBD caused a large increase in MKP-3 expression in trigeminal neurons involved in pain transmission. Generally, the lower concentration of CBD mediated a similar cellular effective when compared to the higher concentration in stimulating MKP expression. While the temporal effects of the CBD on MKP-1 and MKP-2 levels were somewhat variable, the levels of MKP-3 were consistently increased for up to 48 hrs post treatment. Treatment of animals with CBD did not impair cognitive abilities such as novel object recognition and spatial reference memory. In agreement with the behavioral data, significant changes in the levels of MKP-1, MKP-2, or MKP-3 were not observed in the region of the brain containing the hippocampus and dentate gyms.

CONCLUSIONS

It was found that a CBD extract containing very low THC levels did not impair cognitive abilities associated with short-term memory. Importantly, the CBD caused upregulation of MKPs in neuronal cells in the ganglion and spinal cord involved in pain transmission. In particular, the CBD increased neuronal expression of MKP-3, which is a protein that lowers neuronal excitability. These results provide evidence that CBD is effective in blocking and potentially reversing pain mediated by either peripheral or central sensitization—physiological conditions implicated in migraine, TMD, and other neuroinflammatory diseases.

Example 2

Formulation for Lozenges and Fast-Dissolving Lozenges

The formulation shown in Table 1 shows one embodiment of a formula for a fast dissolve lozenge that incorporates cannabinoids (CBD, THC, etc). The MCC and bamboo fiber concentration is increased or decreased relative to the other constituents to alter the dissolution rate of the lozenge, i.e. fast-dissolving, slow dissolving etc. The bulk fillers absorb moisture quickly which creates the dissolution. A "fast dissolving" is generally a tablet that dissolves in less than 1 minute in the oral cavity or sublingually. The other type of lozenge i.e. slower dissolving will dissolve in 3+ minutes as it resides in the mouth.

TABLE 1

| INGREDIENT | FORMULA % |
|---|---|
| Dextrose (sugar) or Sorbitol (sugar free) | 62.37% |
| MCC - Microcrystalline cellulose (bulk filler) | 20.79% |
| Bamboo fibers (bulk filler) | 11.23% |
| Cannabinoid (powder or oil/resin) | 2.49% |
| Flavor powders | 1.25% |
| Stevia (sweetener) | 0.62% |
| Magnesium stearate (tablet flow agent) | 1.25% |
| Total | 100.00% |

What is claimed is:

1. A composition comprising:
    a sugar, sugar alcohol, or sweeteners, and combinations thereof,
    bamboo fibers,
    a cannabinoid,
    flavorings, and
    tableting lubricants or powder flow agents, and combinations thereof, wherein the composition is a powder.

2. The composition of claim 1, wherein the composition, based on the total weight of the composition, comprises:
    about 10% to about 80% by weight of a sugar, sugar alcohol, or sweetener, and combinations thereof,
    about 5% to about 50% by weight of bamboo fibers,
    about 0.1% to about 20% by weight of a cannabinoid,
    about 0.1% to about 10% by weight of flavorings, and
    about 0.1% to about 10% by weight of tableting lubricants or powder flow agents, and combinations thereof.

3. The composition of claim 1, wherein the composition, based on the total weight of the composition, comprises:
    about 55% to about 70% by weight of a sugar, sugar alcohol, or sweetener, and combinations thereof,
    about 5% to about 20% by weight of bamboo fibers,
    about 0.1% to about 10% by weight of a cannabinoid,
    about 0.1% to about 5% by weight of flavorings, and
    about 0.1% to about 5% by weight of tableting lubricants or powder flow agents, and combinations thereof.

4. The composition of claim 1, wherein the sugar comprises dextrose, sucrose or a combination thereof.

5. The composition of claim 1, wherein the sugar alcohol comprises: sorbitol, xylitol, or a combination thereof.

6. The composition of claim 1, wherein the sweetener comprises sucralose or stevia.

7. The composition of claim 1, wherein the tableting lubricants and powder flow agents comprises magnesium stearate, silicon dioxide, calcium stearate, stearic acid, talc or rice bran-based excipients and combinations thereof.

8. A composition consisting of:
    a sugar, sugar alcohol, or sweeteners, and combinations thereof,
    bamboo fibers,
    a cannabinoid,
    flavorings, and
    tableting lubricants and powder flow agents,
    wherein the composition is a powder.

9. The composition of claim 8, wherein the composition, based on the total weight of the composition, consists of:
    about 55% to about 70% by weight of a sugar, sugar alcohol, or sweetener, and combinations thereof,
    about 5% to about 20% by weight of bamboo fibers,
    about 0.1% to about 10% by weight of a cannabinoid,
    about 0.1% to about 5% by weight of flavorings, and
    about 0.1% to about 5% by weight of tableting lubricants and powder flow agents.

10. A composition comprising:
    a sugar, sugar alcohol, or sweeteners, and combinations thereof,
    bamboo fibers,
    a cannabidiol (CBD) or tetrahydrocannabinol (THC), and combinations thereof,
    flavorings,
    tableting lubricants or powder flow agents, and combinations thereof, wherein the composition is a powder.

11. The composition of claim 10, wherein the composition, based on the total weight of the composition, comprises:
    about 10% to about 80% by weight of a sugar, sugar alcohol, or sweetener, and combinations thereof,
    about 5% to about 50% by weight of bamboo fibers,
    about 0.1% to about 20% by weight of a cannabidiol (CBD), a tetrahydrocannabinol (THC) or combinations thereof,
    about 0.1% to about 10% by weight of a flavoring, and
    about 0.1% to about 10% by weight of tableting lubricants and powder flow agents.

12. The composition of claim 10, wherein the composition, based on the total weight of the composition, comprises:
    about 55% to about 70% by weight of a sugar, sugar alcohol, or sweetener, and combinations thereof,
    about 5% to about 20% by weight of bamboo fibers,
    about 0.1% to about 10% by weight of cannabidiol (CBD), tetrahydrocannabinol (THC) or the combination thereof,
    about 0.1% to about 5% by weight of flavorings, and
    about 0.1% to about 5% by weight of tableting lubricants and powder flow agents.

13. The composition of claim 10, wherein the sugar comprises dextrose, sucrose or a combination thereof.

14. The composition of claim 10, wherein the sugar alcohol comprises: sorbitol, xylitol, or a combination thereof.

15. The composition of claim 10, wherein the sweetener comprises sucralose, monk fruit, neotame, aspartame, acesulfame potassium, licorice extract, stevia, honey or agave nectar, or combinations thereof.

16. The composition of claim 10, wherein the tableting lubricants and powder flow agents comprise magnesium stearate, silicon dioxide, calcium stearate, stearic acid, talc or rice bran-based excipients and combinations thereof.

* * * * *